United States Patent [19]

Kita et al.

[11] Patent Number: 5,225,559

[45] Date of Patent: Jul. 6, 1993

[54] DIARYLMETHOXYPIPERIDINE DERIVATIVES

[75] Inventors: Jun'ichiro Kita; Shinji Takamura; Kayoko Yamano; Hiroshi Fujiwara; Hiroko Honda; Kumiko Murata, all of Ube, Japan

[73] Assignee: Ube Industries, Ltd., Yamaguchi, Japan

[21] Appl. No.: 791,512

[22] Filed: Nov. 14, 1991

[30] Foreign Application Priority Data

Nov. 15, 1990 [JP] Japan .................. 2-307190

[51] Int. Cl.$^5$ ............... C07D 211/36; C07D 211/06; C07D 213/04
[52] U.S. Cl. .................... 546/194; 546/196; 546/210; 546/216
[58] Field of Search ............... 546/194, 196, 210, 216

[56] References Cited

U.S. PATENT DOCUMENTS

| 4,200,641 | 4/1980 | Vandenberk | 546/216 |
| 4,550,116 | 10/1985 | Soto et al. | 546/216 |
| 4,929,618 | 5/1990 | Koda et al. | 546/194 |

FOREIGN PATENT DOCUMENTS 61-194068 8/1986 Japan .
1280290 7/1972 United Kingdom .

OTHER PUBLICATIONS

Walsh et al., J. Med. Chem., vol. 32, pp. 105-118 (1989).

*Primary Examiner*—C. Warren Ivy
*Assistant Examiner*—Celia Chang
*Attorney, Agent, or Firm*—Finnegan, Henderson, Farabow, Garrett & Dunner

[57] ABSTRACT

Disclosed is a diarylmethoxypiperidine compound represented by the formula (I):

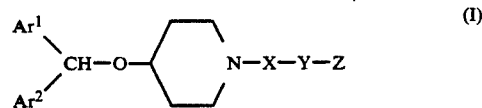

wherein Ar$^1$ and Ar$^2$ each represent a phenyl group which may be substituted by a specific substituent, or a pyridyl group; X represents an alkylene group or a group having

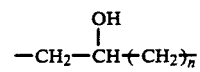

where n represents an integer of 1 to 8; Y represents oxygen atom or a group having —CONH—; and Z represents a phenyl group having at least one specific substituent as defined in the specification; and pharmaceutically acceptable salt thereof.

7 Claims, No Drawings

DIARYLMETHOXYPIPERIDINE DERIVATIVES

BACKGROUND OF THE INVENTION

This invention relates to novel diarylmethoxypiperidine derivatives having antihistaminic action and antileukotrienic action and useful as a pharmaceutical.

Recently, several piperidine derivatives have been described as antiallergic agents. Illustrative of such compounds are those disclosed in Japanese Unexamined Patent Publications No. 94962/1985 and No. 194068/1986, J. Med. Chem. 1989, 32, pp. 105–118 and U.S. Pat. No. 4,929,618.

SUMMARY OF THE INVENTION

For the purpose of developing an antiallergic drug, the present inventors have synthesized diarylmethoxypiperidine derivatives and conducted their pharmacological tests. As a result, they have found that novel compounds having the formula (I) shown below possess pharmacological activities such as antihistaminic action and antileukotrienic action and also that the compounds are low in toxicity, and recognized that the compounds are useful as an antiallergic drug, to accomplish the present invention.

The diarylmethoxypiperidine derivatives of the present invention are compounds represented by the formula (I):

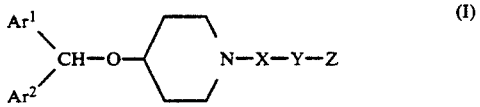

wherein $Ar^1$ and $Ar^2$ each represent a phenyl group which may be substituted by a halogen, nitro, a lower alkyl, a lower alkoxy or a halo-lower alkyl or a pyridyl group; X represents an alkylene group having 1 to 10 carbon atoms or a group having

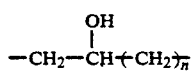

where n represents an integer of 1 to 8; Y represents oxygen atom or a group having —CONH—; and Z represents a phenyl group having at least one substituent selected from the group consisting of a halogen, a lower alkyl, a lower alkenyl, a lower alkoxy, hydroxy, cyano, carboxyl, a lower alkoxycarbonyl, an alkanoyl, an alkanoylamino, methylenedioxy, tetrazolyl, —CONHR$^1$ and —Q—COOR$^2$ (where R$^1$ represents hydrogen atom, a lower alkyl group, a cycloalkyl group, a benzenesulfonyl group, a tetrazolyl group or a group having the formula (B) shown below; Q represents a lower alkylene group or a lower alkenylene group; and R$^2$ represents hydrogen atom or a lower alkyl group), or a group having the formula:

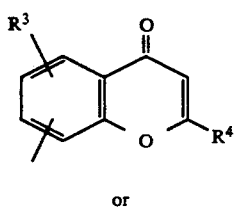

or

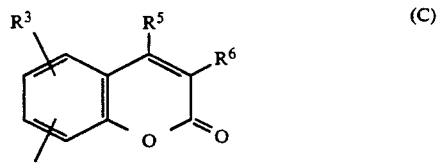

where R$^3$ represents hydrogen atom, a lower alkyl group, a lower alkenyl group, a lower alkoxy group or hydroxyl group; R$^4$ represents carboxyl group, a lower alkoxycarbonyl group, cyano group, phenyl group, a carbamoyl group or a tetrazolyl group; R$^5$ represents hydrogen atom or a lower alkyl group; and R$^6$ represents hydrogen atom or a lower alkoxycarbonyl group; and pharmaceutically acceptable salts thereof.

DESCRIPTION OF THE PREFERRED EMBODIMENTS

In the following, the present invention is explained in detail.

In the above formula (I), $Ar^1$ and $Ar^2$ may preferably include phenyl group; a phenyl group substituted by a halogen atom such as 4-fluorophenyl, 2-, 3- or 4-chlorophenyl, 2- or 4-bromophenyl and 2- or 4-iodophenyl; a phenyl group substituted by an alkyl group having 1 to 4 carbon atoms such as 2-, 3- or 4-methylphenyl, 2,4- or 3,4-dimethylphenyl, 4-ethylphenyl, 4-isopropylphenyl, 4-n-propylphenyl and 4-n-butylphenyl; a phenyl group substituted by a trifluoromethyl group such as 2-, 3- or 4-trifluoromethylphenyl; a phenyl group substituted by an alkoxy group having 1 to 3 carbon atoms such as 4-methoxyphenyl, 2,4- or 3,4-dimethoxyphenyl, 4-ethoxyphenyl and 4-n-propoxyphenyl; a phenyl group substituted by nitro group such as 2-, 3- or 4-nitrophenyl; and a pyridyl group such as 2-, 3- or 4pyridyl.

X may preferably include a straight or branched alkylene group having 1 to 10 carbon atoms such as methylene, ethylene, trimethylene, tetramethylene, pentamethylene, hexamethylene, heptamethylene, octamethylene, nonamethylene, decamethylene, 1-methylethylene, 2-methylethylene, 1-methyltrimethylene, 2-methyltrimethylene, 3-methyltrimethylene, 1-methyltetramethylene, 2-methyltetramethylene, 3-methyltetramethylene and 4-methyltetramethylene; and a group having

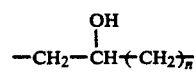

such as 2-hydroxytrimethylene and 2-hydroxytetramethylene.

Z represents a phenyl group having at least one of the following substituents: a halogen atom such as fluorine, chlorine, bromine and iodine; an alkyl group having 1 to 4 carbon atoms such as methyl, ethyl, n-propyl, isopropyl, n-butyl, isobutyl, sec-butyl and t-butyl; an alkenyl group having 2 to 4 carbon atoms such as vinyl, allyl, 1-butenyl, 2-butenyl and 3-butenyl; an alkoxy group having 1 to 3 carbon atoms such as methoxy, ethoxy, n-propoxy and isopropoxy; hydroxyl group; cyano group; carboxyl group; an alkoxycarbonyl group having 2 to 5 carbon atoms such as methoxycarbonyl, ethoxycarbonyl, n-propoxycarbonyl, isopropoxycarbonyl, n-butoxycarbonyl, isobutoxycarbonyl, secbutoxycarbonyl and t-butoxycarbonyl; an alkanoyl group having 1 to 4 carbon atoms such as formyl, acetyl, propionyl, n-butyryl and isobutyryl; an alkanoylamino group having 1 to 4 carbon atoms such as formylamino, acetylamino, propionylamino, n-butyrylamino and isobutyrylamino; methylenedioxy group; tetrazol-5-yl group; carbamoyl group; a carbamoyl group substituted by an alkyl group having 1 to 4 carbon atoms such as methyl, ethyl, n-propyl, isopropyl, n-butyl, isobutyl, sec-butyl and t-butyl; a carbamoyl group substituted by a cycloalkyl group having 3 to 6 carbon atoms such as cyclopropyl, cyclopentyl and cyclohexyl; a carbamoyl group substituted by benzenesulfonyl; a carbamoyl group substituted by tetrazol-5-yl; a carbamoyl group substituted by 6-methoxy-2-methoxycarbonyl-chromon-8-yl; a group having —Q—COOR² (where Q represents an alkylene group having 1 to 3 carbon atoms such as methylene, ethylene and trimethylene or an alkenylene group having 1 to 3 carbon atoms such as vinylene, 1-propenylene and 2-propenylene; R² represents hydrogen atom or an alkyl group having 1 to 4 carbon atoms such as methyl, ethyl, n-propyl, isopropyl, n-butyl, isobutyl, sec-butyl and t-butyl); and a group having the formula:

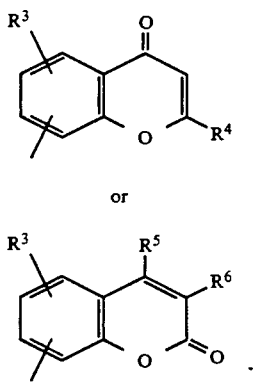

where R³ represents hydrogen atom; an alkyl group having 1 to 3 carbon atoms such as methyl, ethyl, n-propyl and isopropyl; an alkenyl group having 3 to 4 carbon atoms such as allyl, 1-butenyl, 2-butenyl and 3-butenyl; an alkoxy group having 1 to 3 carbon atoms such as methoxy, ethoxy, n-propoxy and isopropoxy; or hydroxyl group; R⁴ represents carboxyl group; an alkoxycarbonyl group having 2 to 5 carbon atoms such as methoxycarbonyl, ethoxycarbonyl, n-propoxycarbonyl, isopropoxycarbonyl, n-butoxycarbonyl, isobutoxycarbonyl, sec-butoxycarbonyl and t-butoxycarbonyl, cyano group; phenyl group; carbamoyl group; or tetrazol-5-yl group; R⁵ represents hydrogen atom or an alkyl group having 1 to 4 carbon atoms such as methyl, ethyl, n-propyl, isopropyl, n-butyl, isobutyl, sec-butyl and t-butyl; and R⁶ represents hydrogen atom or an alkoxycarbonyl group having 2 to 5 carbon atoms such as methoxycarbonyl, ethoxycarbonyl, n-propoxycarbonyl, isopropoxycarbonyl, n-butoxycarbonyl, isobutoxycarbonyl, sec-butoxycarbonyl and t-butoxycarbonyl.

As further preferred compounds in the above formula (I), there may be mentioned compounds in which Ar¹ and Ar² each represent phenyl group, 4-chlorophenyl group, 4-fluorophenyl group or 2-pyridyl group; X represents ethylene group, trimethylene group or 2-hydroxytrimethylene group; Y represents oxygen atom or a group having —CONH—; and Z represents 4-t-butylphenyl group, 4-methoxycarbonylphenyl group, 4-(tetrazol-5-yl)phenyl group, 4-acetyl-2-methoxyphenyl group, 4-acetyl-2,6-dimethoxyphenyl group, 4-acetyl3-hydroxyphenyl group, 3-acetyl-4-hydroxyphenyl group, 3-acetyl-5-fluoro-2-hydroxyphenyl group, 4-acetyl-2-allyl-3 -hydroxyphenyl group, 4-acetyl-3-hydroxy-2-n-propylphenyl group, 2-methoxy-4-methoxycarbonylphenyl group, 3-hydroxy-4-methoxycarbonylphenyl group, 4-[N-(tetrazol-5-yl)carbaphenyl group, 2-carboxy-8-n-propylchromon-7-yl group, 8-allyl-2-n-butoxycarbonylchromon-7-yl group, 8-allyl-2-carbamoylchromon-7-yl group, 8-allyl-2-cyanochromon-7-yl group, 8-allyl-2-(tetrazol-5-yl)chromon-7-yl group, 2-methoxycarbonyl-6-methylchromon-8-yl group, 2-methoxycarbonyl -6-isopropylchromon-8-yl group, 8-allyl-4-methylcoumarin-7-yl group or 6-methoxycoumarin-7-yl group.

The compounds having the above formula (I) can be made into pharmaceutically acceptable salts, if necessary.

As such salts, there may be mentioned acid addition salts of mineral acids such as hydrochloride, hydrobromide, hydroiodide, sulfate and phosphate; acid addition salts of organic acids such as benzoate, methanesulfonate, ethanesulfonate, benzenesulfonate, p-toluenesulfonate, oxalate, maleate, fumarate, tartarate and citrate; and metal salts such as sodium salt, potassium salt, calcium salt, magnesium salt, manganese salt, iron salt and aluminum salt.

The compounds (I) of the present invention can exist also as hydrates.

As the compounds having the formula (I) of the present invention, there may be mentioned compounds exemplified in Table 1 and pharmaceutically acceptable salts thereof.

TABLE 1

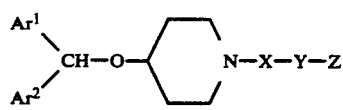

| Compound No. | Ar¹ | Ar² | X | Y | Z |
|---|---|---|---|---|---|
| 1 | phenyl | phenyl | —(CH₂)₃— | —O— | 2-OCH₃, 4-COCH₃-phenyl |

TABLE 1-continued
$$\begin{array}{c} Ar^1 \\ \phantom{Ar^1}CH-O-\phantom{X}N-X-Y-Z \\ Ar^2 \end{array}$$
| Compound No. | Ar¹ | Ar² | X | Y | Z |
|---|---|---|---|---|---|
| 2 | 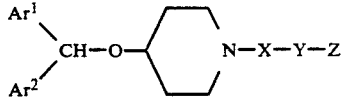 |  | —(CH₂)₃— | —O— | 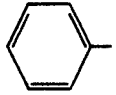 |
| 3 | 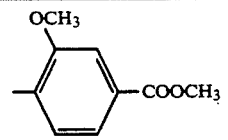 | 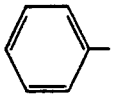 | —(CH₂)₃— | —O— | 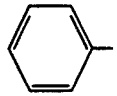 |
| 4 | 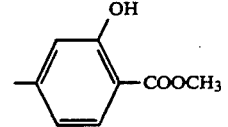 | 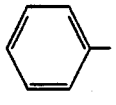 | —(CH₂)₃— | —O— | 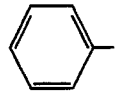 |
| 5 | 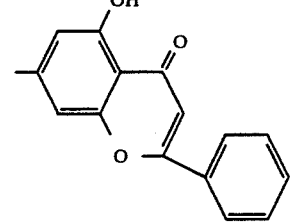 | 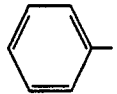 | —(CH₂)₃— | —O— |  |
| 6 | 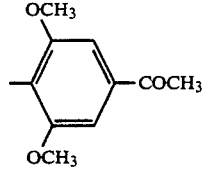 |  | —(CH₂)₃— | —O— |  |
| 7 | 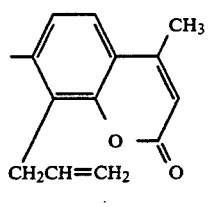 |  | —(CH₂)₃— | —O— |  |
| 8 | 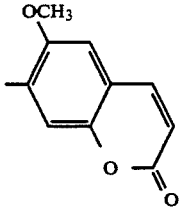 |  | —(CH₂)₃— | —O— |  |
| 9 | 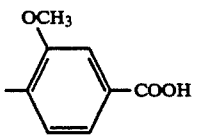 |  | —(CH₂)₃— | —O— |  |

TABLE 1-continued
| Compound No. | Ar¹ | Ar² | X | Y | Z |
|---|---|---|---|---|---|
| 10 | 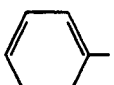 | 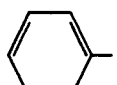 | —(CH$_2$)$_3$— | —O— | 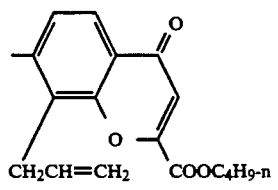 |
| 11 | 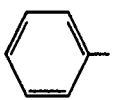 | 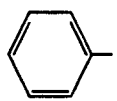 | —(CH$_2$)$_3$— | —O— | 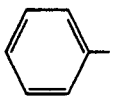 |
| 12 | 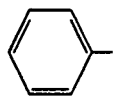 | 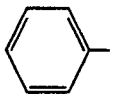 | —(CH$_2$)$_3$— | —O— | 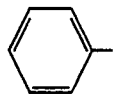 |
| 13 | 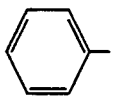 | 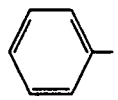 | —(CH$_2$)$_3$— | —O— | 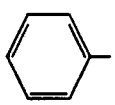 |
| 14 | 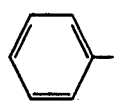 | 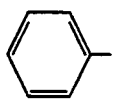 | —(CH$_2$)$_3$— | —O— | 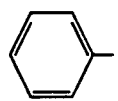 |
| 15 | 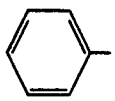 |  | —(CH$_2$)$_3$— | —O— | |
| 16 | | | —(CH$_2$)$_3$— | —O— | |
| 17 | | | —(CH$_2$)$_3$— | —O— | |

TABLE 1-continued $$\text{Ar}^1\text{Ar}^2\text{CH}-\text{O}-\text{[piperidine]}-\text{N}-\text{X}-\text{Y}-\text{Z}$$

| Compound No. | Ar¹ | Ar² | X | Y | Z |
|---|---|---|---|---|---|
| 18 | C₆H₅- | C₆H₅- | -(CH₂)₃- | -O- | 4-(C(CH₃)₃)C₆H₄- |
| 19 | C₆H₅- | C₆H₅- | -(CH₂)₃- | -O- | 4-(COOCH₃)C₆H₄- |
| 20 | C₆H₅- | C₆H₅- | -(CH₂)₃- | -O- | 3-OCH₃-4-(CH=CH-COOH)C₆H₃- |
| 21 | C₆H₅- | C₆H₅- | -(CH₂)₃- | -O- | 4-(tetrazol-5-yl)C₆H₄- |
| 22 | 4-F-C₆H₄- | 4-F-C₆H₄- | -CH₂CH(OH)CH₂- | -O- | 2-OH-3-(n-C₃H₇)-6-(COCH₃)C₆H₂- |
| 23 | 4-F-C₆H₄- | 4-F-C₆H₄- | -(CH₂)₃- | -O- | 3-(n-C₃H₇)-[furanone-COOH substituted phenyl] |
| 24 | 4-F-C₆H₄- | 4-F-C₆H₄- | -(CH₂)₃- | -O- | 3-OCH₃-4-(COCH₃)C₆H₃- |
| 25 | 4-F-C₆H₄- | 4-F-C₆H₄- | -(CH₂)₃- | -O- | 4-(COOCH₃)C₆H₄- |
| 26 | 4-F-C₆H₄- | 4-F-C₆H₄- | -(CH₂)₃- | -O- | 4-(COOH)C₆H₄- |

TABLE 1-continued
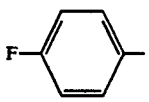
| Compound No. | Ar¹ | Ar² | X | Y | Z |
|---|---|---|---|---|---|
| 27 | 4-F-C₆H₄- | 4-F-C₆H₄- | —(CH₂)₃— | —O— | 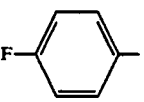 |
| 28 | 4-F-C₆H₄- | 4-F-C₆H₄- | —(CH₂)₃— | —O— | 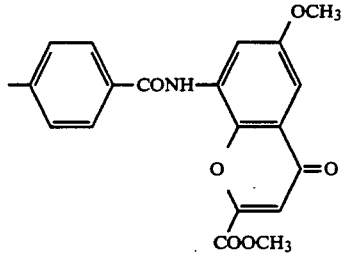 |
| 29 | 4-F-C₆H₄- | 4-F-C₆H₄- | —(CH₂)₃— | —O— | 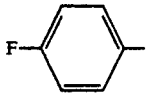 |
| 30 | 4-F-C₆H₄- | 4-F-C₆H₄- | —(CH₂)₃— | —O— | 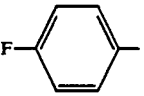 |
| 31 | 4-F-C₆H₄- | 4-F-C₆H₄- | —(CH₂)₃— | —O— | 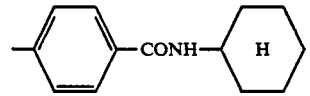 |
| 32 | 4-F-C₆H₄- | 4-F-C₆H₄- | —(CH₂)₃— | —CONH— | 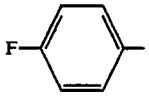 |
| 33 | 4-F-C₆H₄- | 4-F-C₆H₄- | —(CH₂)₃— | —CONH— | 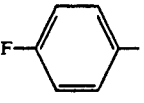 |
| 34 | 4-F-C₆H₄- | 4-F-C₆H₄- | —(CH₂)₃— | —CONH— | 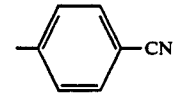 |

TABLE 1-continued $$\begin{array}{c}Ar^1\\ \phantom{Ar^1}\diagdown\\CH-O-\!\!\underset{\phantom{X}}{\bigcirc}\!\!-N-X-Y-Z\\ \phantom{Ar^2}\diagup\\Ar^2\end{array}$$

| Compound No. | Ar¹ | Ar² | X | Y | Z |
|---|---|---|---|---|---|
| 35 | 4-F-C₆H₄ | 4-F-C₆H₄ | —(CH₂)₃— | —CONH— | (isopropyl/methyl-substituted chromone-carboxylate) |
| 36 | 4-F-C₆H₄ | 4-F-C₆H₄ | —(CH₂)₃— | —CONH— | 4-COOCH₃-C₆H₄ |
| 37 | 4-F-C₆H₄ | 4-F-C₆H₄ | —(CH₂)₃— | —CONH— | 4-COOH-C₆H₄ |
| 38 | 4-Cl-C₆H₄ | 2-pyridyl | —(CH₂)₂— | —O— | 2-OCH₃-C₆H₄ |
| 39 | 4-Cl-C₆H₄ | 2-pyridyl | —(CH₂)₂— | —O— | 4-I-C₆H₄ |
| 40 | 4-Cl-C₆H₄ | 2-pyridyl | —(CH₂)₂— | —O— | 4-OCH₃-C₆H₄ |
| 41 | 4-Cl-C₆H₄ | 2-pyridyl | —(CH₂)₂— | —O— | 3-OCH₃-C₆H₄ |
| 42 | 4-Cl-C₆H₄ | 2-pyridyl | —(CH₂)₂— | —O— | 2,5-(CH₃)₂-C₆H₃ |
| 43 | 4-Cl-C₆H₄ | 2-pyridyl | —(CH₂)₂— | —O— | 4-Cl-C₆H₄ |

TABLE 1-continued $$\begin{array}{c} Ar^1 \\ \phantom{Ar^2}\diagdown \\ Ar^2 \diagup CH-O-\!\!\!\!\bigcirc\!\!\!\!-N-X-Y-Z \end{array}$$

| Compound No. | Ar¹ | Ar² | X | Y | Z |
|---|---|---|---|---|---|
| 44 | 4-Cl-C₆H₄- | 2-pyridyl | —(CH₂)₂— | —O— | 3,4-methylenedioxyphenyl |
| 45 | 4-Cl-C₆H₄- | 2-pyridyl | —(CH₂)₂— | —O— | 3,5-dimethoxyphenyl |
| 46 | 4-Cl-C₆H₄- | 2-pyridyl | —(CH₂)₂— | —O— | 4-cyanophenyl |
| 47 | 4-Cl-C₆H₄- | 2-pyridyl | —(CH₂)₂— | —O— | 4-acetylphenyl |
| 48 | 4-Cl-C₆H₄- | 2-pyridyl | —(CH₂)₂— | —O— | 3-chlorophenyl |
| 49 | 4-Cl-C₆H₄- | 2-pyridyl | —CH₂CH(OH)CH₂— | —O— | 2-acetyl-3-n-propyl-6-hydroxyphenyl |
| 50 | 4-Cl-C₆H₄- | 2-pyridyl | —(CH₂)₃— | —O— | 2-acetyl-3-n-propyl-6-hydroxyphenyl |
| 51 | 4-Cl-C₆H₄- | 2-pyridyl | —(CH₂)₃— | —O— | (see structure) |
| 52 | 4-Cl-C₆H₄- | 2-pyridyl | —(CH₂)₂— | —O— | 2-acetyl-3-n-propyl-6-hydroxyphenyl |

TABLE 1-continued

Ar¹\\
    CH—O—[piperidine]—N—X—Y—Z\\
Ar²

| Compound No. | Ar¹ | Ar² | X | Y | Z |
|---|---|---|---|---|---|
| 53 | 4-Cl-C₆H₄- | 2-pyridyl | -CH₂CH(OH)CH₂- | -O- | 4-COCH₃, 2-OH-phenyl |
| 54 | 4-Cl-C₆H₄- | 2-pyridyl | -(CH₂)₅- | -O- | 4-COCH₃, 2-OH, 3-n-C₃H₇-phenyl |
| 55 | 4-Cl-C₆H₄- | 2-pyridyl | -(CH₂)₆- | -O- | 4-COCH₃, 2-OH, 3-n-C₃H₇-phenyl |
| 56 | 4-Cl-C₆H₄- | 2-pyridyl | -(CH₂)₁₀- | -O- | 4-COCH₃, 2-OH, 3-n-C₃H₇-phenyl |
| 57 | 4-Cl-C₆H₄- | 2-pyridyl | -CH₂CH(OH)CH₂- | -O- | 4-COCH₃, 2-OH, 3-CH₂CH=CH₂-phenyl |
| 58 | 4-Cl-C₆H₄- | 2-pyridyl | -(CH₂)₃- | -O- | 4-COCH₃, 2-OH, 3-CH₂CH=CH₂-phenyl |
| 59 | 4-Cl-C₆H₄- | 2-pyridyl | -(CH₂)₃- | -O- | 4-COCH₃, 3-OCH₃-phenyl |
| 60 | 4-Cl-C₆H₄- | 2-pyridyl | -(CH₂)₃- | -O- | 4-COOCH₃-phenyl |
| 61 | 4-Cl-C₆H₄- | 2-pyridyl | -(CH₂)₃- | -O- | 4-CONH-(1H-tetrazol-5-yl)-phenyl |

TABLE 1-continued

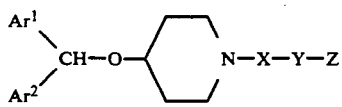

| Compound No. | Ar¹ | Ar² | X | Y | Z |
|---|---|---|---|---|---|
| 62 | 4-Cl-C₆H₄- | 2-pyridyl | —(CH₂)₂— | —O— | 4-(1H-tetrazol-5-yl)phenyl |
| 63 | 4-Cl-C₆H₄- | 2-pyridyl | —(CH₂)₃— | —CONH— | 5-methoxy-3-methyl-2-(methoxycarbonyl... chromone derivative) |
| 64 | 4-Cl-C₆H₄- | 2-pyridyl | —(CH₂)₃— | —CONH— | 3-acetyl-2-hydroxy-5-methylphenyl |
| 65 | 4-Cl-C₆H₄- | 2-pyridyl | —(CH₂)₃— | —CONH— | 3-acetyl-4-hydroxyphenyl |
| 66 | 4-Cl-C₆H₄- | 2-pyridyl | —(CH₂)₃— | —CONH— | 3-acetyl-2-hydroxy-5-methylphenyl |
| 67 | 4-Cl-C₆H₄- | 2-pyridyl | —(CH₂)₃— | —CONH— | chromone-methoxycarbonyl derivative |
| 68 | 4-Cl-C₆H₄- | 2-pyridyl | —(CH₂)₃— | —CONH— | 3-acetyl-5-fluoro-2-hydroxyphenyl |

TABLE 1-continued $$\begin{array}{c}\text{Ar}^1\\\text{CH—O}\phantom{xxxxx}\text{N—X—Y—Z}\\\text{Ar}^2\end{array}$$

| Compound No. | Ar¹ | Ar² | X | Y | Z |
|---|---|---|---|---|---|
| 69 | 4-Cl-C₆H₄– | 2-pyridyl | –(CH₂)₅– | –CONH– | 2-OH, 5-COCH₃-C₆H₃– |
| 70 | 4-Cl-C₆H₄– | 2-pyridyl | –(CH₂)₃– | –CONH– | 2-COCH₃, 4-OH-C₆H₃– |
| 71 | 4-Cl-C₆H₄– | C₆H₅– | –(CH₂)₃– | –O– | 3-OCH₃, 4-COCH₃-C₆H₃– |
| 72 | 4-Cl-C₆H₄– | C₆H₅– | –(CH₂)₃– | –O– | 3-OCH₃, 4-COOCH₃-C₆H₃– |
| 73 | 4-Cl-C₆H₄– | C₆H₅– | –(CH₂)₃– | –O– | 2-OH, 4-COOCH₃-C₆H₃– |
| 74 | 4-Cl-C₆H₄– | C₆H₅– | –(CH₂)₃– | –O– | flavone derivative |
| 75 | 4-Cl-C₆H₄– | C₆H₅– | –(CH₂)₃– | –O– | 3,5-di-OCH₃, 4-COCH₃-C₆H₂– |
| 76 | 4-Cl-C₆H₄– | C₆H₅– | –(CH₂)₃– | –O– | allyl-substituted chromone derivative |

TABLE 1-continued $$\begin{array}{c}\text{Ar}^1\\\text{CH-O-}\bigcirc\text{N-X-Y-Z}\\\text{Ar}^2\end{array}$$

| Compound No. | Ar¹ | Ar² | X | Y | Z |
|---|---|---|---|---|---|
| 77 | 4-Cl-C₆H₄ | C₆H₅ | —(CH₂)₃— | —O— | 6-methoxy-7-methyl-coumarin-3-yl |
| 78 | 4-Cl-C₆H₄ | C₆H₅ | —(CH₂)₃— | —O— | 3-methoxy-4-methyl-benzoic acid |
| 79 | 4-Cl-C₆H₄ | 4-Cl-C₆H₄ | —(CH₂)₃— | —O— | 3-methoxy-4-methyl-N-(phenylsulfonyl)benzamide |
| 80 | 4-Cl-C₆H₄ | 4-Cl-C₆H₄ | —(CH₂)₃— | —O— | n-butyl ester of allyl-methyl-chromone carboxylic acid |
| 81 | 4-Cl-C₆H₄ | 4-Cl-C₆H₄ | —(CH₂)₃— | —O— | allyl-methyl-chromone carboxamide |
| 82 | 4-Cl-C₆H₄ | 4-Cl-C₆H₄ | —(CH₂)₃— | —O— | allyl-methyl-chromone carbonitrile |
| 83 | 4-Cl-C₆H₄ | 4-Cl-C₆H₄ | —(CH₂)₃— | —O— | 4-cyanophenyl |
| 84 | 4-Cl-C₆H₄ | 4-Cl-C₆H₄ | —(CH₂)₃— | —O— | allyl-methyl-chromone tetrazolyl |

TABLE 1-continued $$\text{Ar}^1\text{Ar}^2\text{CH-O-}\underset{\text{piperidine}}{\bigcirc}\text{-N-X-Y-Z}$$

| Compound No. | Ar¹ | Ar² | X | Y | Z |
|---|---|---|---|---|---|
| 85 | 4-Cl-C₆H₄- | 4-Cl-C₆H₄- | -(CH₂)₃- | -O- | 2-OH, 3-CH₂CH=CH₂, 6-COOCH₃ phenyl |
| 86 | 4-Cl-C₆H₄- | 4-Cl-C₆H₄- | -(CH₂)₃- | -O- | 2-OH, 3-CH₂CH=CH₂, 6-CONHCH(CH₃)₂ phenyl |
| 87 | 4-F-C₆H₄- | C₆H₅- | -(CH₂)₃- | -O- | 2-(O-C(=O)-)-, 3-CH=C(COOC₂H₅)- phenyl (coumarin-3-carboxylate) |
| 88 | 4-F-C₆H₄- | C₆H₅- | -(CH₂)₃- | -O- | 4-C(CH₃)₃-phenyl |
| 89 | 4-F-C₆H₄- | C₆H₅- | -(CH₂)₃- | -O- | 4-COOCH₃-phenyl |
| 90 | 4-F-C₆H₄- | C₆H₅- | -(CH₂)₃- | -O- | 3-OCH₃, 4-CH=CH-COOCH₃ phenyl |
| 91 | 4-F-C₆H₄- | C₆H₅- | -(CH₂)₃- | -O- | 4-(1H-tetrazol-5-yl)phenyl |
| 92 | 4-CF₃-C₆H₄- | C₆H₅- | -CH₂CH(OH)CH₂- | -O- | 2-OH, 3-n-C₃H₇, 6-COCH₃ phenyl |
| 93 | 4-CF₃-C₆H₄- | C₆H₅- | -(CH₂)₃- | -O- | 2-(O-C(=O)-CH=)- , 3-n-C₃H₇, 6-CO- phenyl (with COOH) |

TABLE 1-continued

Structure: Ar¹Ar²CH—O—(piperidine)—N—X—Y—Z

| Compound No. | Ar¹ | Ar² | X | Y | Z |
|---|---|---|---|---|---|
| 94 | 4-CF₃-C₆H₄– | C₆H₅– | –(CH₂)₃– | –O– | 3-OCH₃-4-COCH₃-C₆H₃– |
| 95 | 4-CF₃-C₆H₄– | 4-CF₃-C₆H₄– | –(CH₂)₃– | –O– | 4-COOCH₃-C₆H₄– |
| 96 | 4-CF₃-C₆H₄– | 4-CF₃-C₆H₄– | –(CH₂)₃– | –O– | 4-COOH-C₆H₄– |
| 97 | 4-CF₃-C₆H₄– | 4-CF₃-C₆H₄– | –(CH₂)₃– | –O– | substituted phenyl with CONH, OCH₃, COOCH₃ and enol-ketone moiety |
| 98 | 4-CF₃-C₆H₄– | 4-CF₃-C₆H₄– | –(CH₂)₃– | –O– | 4-(CONH-cyclohexyl)-C₆H₄– |
| 99 | 4-CF₃-C₆H₄– | 4-CF₃-C₆H₄– | –(CH₂)₃– | –O– | 4-CN-C₆H₄– |
| 100 | 4-CF₃-C₆H₄– | 4-CF₃-C₆H₄– | –(CH₂)₃– | –O– | 4-C(CH₃)₃-C₆H₄– |
| 101 | 4-CF₃-C₆H₄– | 4-CF₃-C₆H₄– | –(CH₂)₃– | –O– | 4-(1H-tetrazol-5-yl)-C₆H₄– |
| 102 | 4-NO₂-C₆H₄– | C₆H₅– | –(CH₂)₃– | –CONH– | 3-NHCOCH₃-5-COCH₃-4-OH-C₆H₂– |

TABLE 1-continued $$\begin{matrix} Ar^1 \\ Ar^2 \end{matrix} CH-O-\bigcirc-N-X-Y-Z$$

| Compound No. | Ar¹ | Ar² | X | Y | Z |
|---|---|---|---|---|---|
| 103 | 4-NO₂-C₆H₄- | C₆H₅- | -(CH₂)₃- | -CONH- | 2-hydroxy-3-acetyl-5-isopropyl-6-methylphenyl |
| 104 | 4-NO₂-C₆H₄- | C₆H₅- | -(CH₂)₃- | -CONH- | 2-hydroxy-3-acetyl-5-methoxy-6-methylphenyl |
| 105 | 4-NO₂-C₆H₄- | C₆H₅- | -(CH₂)₃- | -CONH- | (4-isopropyl-2,6-dimethyl-3-(methoxycarbonyl-acetyl)phenyl, chromone-type) |
| 106 | 4-NO₂-C₆H₄- | C₆H₅- | -(CH₂)₃- | -CONH- | 4-COOCH₃-C₆H₄- |
| 107 | 4-NO₂-C₆H₄- | C₆H₅- | -(CH₂)₃- | -CONH- | 4-COOH-C₆H₄- |
| 108 | 4-CH₃-C₆H₄- | 2-pyridyl | -(CH₂)₂- | -O- | 2-OCH₃-C₆H₄- |
| 109 | 4-CH₃-C₆H₄- | 2-pyridyl | -(CH₂)₂- | -O- | 4-I-C₆H₄- |
| 110 | 4-CH₃-C₆H₄- | 2-pyridyl | -(CH₂)₂- | -O- | 4-OCH₃-C₆H₄- |
| 111 | 4-CH₃-C₆H₄- | 2-pyridyl | -(CH₂)₂- | -O- | 3-OCH₃-C₆H₄- |

TABLE 1-continued

Ar¹—CH(Ar²)—O—[piperidine]—N—X—Y—Z

| Compound No. | Ar¹ | Ar² | X | Y | Z |
|---|---|---|---|---|---|
| 112 | 4-CH₃-C₆H₄- | 2-pyridyl | —(CH₂)₂— | —O— | 2,4-(CH₃)₂-C₆H₃- |
| 113 | 4-CH₃-C₆H₄- | 2-pyridyl | —(CH₂)₂— | —O— | 4-Cl-C₆H₄- |
| 114 | 4-CH₃-C₆H₄- | 2-pyridyl | —(CH₂)₂— | —O— | 3,4-methylenedioxyphenyl |
| 115 | 4-CH₃-C₆H₄- | 2-pyridyl | —(CH₂)₂— | —O— | 3,5-(OCH₃)₂-C₆H₃- |
| 116 | 4-CH₃-C₆H₄- | 2-pyridyl | —(CH₂)₂— | —O— | 4-CN-C₆H₄- |
| 117 | 4-CH₃-C₆H₄- | 2-pyridyl | —(CH₂)₂— | —O— | 4-COCH₃-C₆H₄- |
| 118 | 4-CH₃-C₆H₄- | 2-pyridyl | —(CH₂)₂— | —O— | 3-Cl-C₆H₄- |
| 119 | 4-CH₃-C₆H₄- | 2-pyridyl | —CH₂CH(OH)CH₂— | —O— | 4-COCH₃-2-OH-3-(n-C₃H₇)-C₆H₂- |
| 120 | 4-CH₃-C₆H₄- | 2-pyridyl | —(CH₂)₃— | —O— | 4-COCH₃-2-OH-3-(n-C₃H₇)-C₆H₂- |

TABLE 1-continued $$\text{Ar}^1\text{Ar}^2\text{CH-O-}\underset{\text{piperidine}}{\diamondsuit}\text{-N-X-Y-Z}$$

| Compound No. | Ar¹ | Ar² | X | Y | Z |
|---|---|---|---|---|---|
| 121 | 4-CH₃-C₆H₄- | 2-pyridyl | -(CH₂)₃- | -O- | 4-methyl-3-(n-C₃H₇)-2-oxo-benzoyl-CH=CH-COOH |
| 122 | 4-CF₃-C₆H₄- | 2-pyridyl | -(CH₂)₂- | -O- | 4-methyl-3-(n-C₃H₇)-2-OH-C₆H₂-COCH₃ |
| 123 | 4-CH₃-C₆H₄- | 2-pyridyl | -CH₂CH(OH)CH₂- | -O- | 4-methyl-2-OH-C₆H₃-COCH₃ |
| 124 | 4-CF₃-C₆H₄- | 2-pyridyl | -(CH₂)₅- | -O- | 4-methyl-3-(n-C₃H₇)-2-OH-C₆H₂-COCH₃ |
| 125 | 4-CF₃-C₆H₄- | 2-pyridyl | -(CH₂)₆- | -O- | 4-methyl-3-(n-C₃H₇)-2-OH-C₆H₂-COCH₃ |
| 126 | 4-CF₃-C₆H₄- | 2-pyridyl | -(CH₂)₁₀- | -O- | 4-methyl-3-(n-C₃H₇)-2-OH-C₆H₂-COCH₃ |
| 127 | 4-CF₃-C₆H₄- | 2-pyridyl | -CH₂CH(OH)CH₂- | -O- | 4-methyl-3-(CH₂CH=CH₂)-2-OH-C₆H₂-COCH₃ |
| 128 | 4-CF₃-C₆H₄- | 2-pyridyl | -(CH₂)₃- | -O- | 4-methyl-3-(CH₂CH=CH₂)-2-OH-C₆H₂-COCH₃ |
| 129 | 4-CF₃-C₆H₄- | 2-pyridyl | -(CH₂)₃- | -O- | 4-methyl-3-OCH₃-C₆H₃-COCH₃ |

TABLE 1-continued $$\text{Ar}^1\text{Ar}^2\text{CH-O-}\underset{\text{piperidine}}{\bigcirc}\text{N-X-Y-Z}$$

| Compound No. | Ar¹ | Ar² | X | Y | Z |
|---|---|---|---|---|---|
| 130 | 4-CF₃-C₆H₄- | 2-pyridyl | -(CH₂)₃- | -O- | 4-(COCH₃)-C₆H₄- |
| 131 | 4-CF₃-C₆H₄- | 2-pyridyl | -(CH₂)₃- | -O- | 4-(CONH-tetrazol-5-yl)-C₆H₄- |
| 132 | 4-CF₃-C₆H₄- | 2-pyridyl | -(CH₂)₂- | -O- | 4-(tetrazol-5-yl)-C₆H₄- |
| 133 | 4-CH₃O-C₆H₄- | 2-pyridyl | -(CH₂)₃- | -CONH- | 5-methoxy-2-(COCH=C(COOCH₃)-O-)-phenyl (chromone-type) |
| 134 | 4-CH₃O-C₆H₄- | 2-pyridyl | -(CH₂)₃- | -CONH- | 3,5-dimethyl-2-hydroxy-4-(COCH₃)-phenyl |
| 135 | 4-CH₃O-C₆H₄- | 2-pyridyl | -(CH₂)₃- | -CONH- | 3-hydroxy-4-(COCH₃)-phenyl |
| 136 | 4-CH₃O-C₆H₄- | 2-pyridyl | -(CH₂)₃- | -CONH- | 3,5-dimethyl-4-hydroxy-2-(COCH₃)-phenyl (substituted) |
| 137 | 4-CH₃O-C₆H₄- | 2-pyridyl | -(CH₂)₃- | -CONH- | methyl-substituted chromone with COOCH₃ |

TABLE 1-continued $$\underset{Ar^2}{\overset{Ar^1}{>}}CH-O-\underset{}{\overset{}{\bigcirc}}N-X-Y-Z$$

| Compound No. | Ar¹ | Ar² | X | Y | Z |
|---|---|---|---|---|---|
| 138 | CH₃O-C₆H₄- | 2-pyridyl | $-(CH_2)_3-$ | $-CONH-$ | 4-F, 2-OH, 6-COCH₃-phenyl |
| 139 | CH₃O-C₆H₄- | 2-pyridyl | $-(CH_2)_5-$ | $-CONH-$ | 3-OH, 4-COCH₃-phenyl |
| 140 | CH₃O-C₆H₄- | 2-pyridyl | $-(CH_2)_3-$ | $-CONH-$ | 3-COCH₃, 4-OH-phenyl |

Of these compounds, preferred compounds are Compounds Nos. 1, 2, 3, 5, 7, 13, 18, 19, 24, 25, 26, 30, 35, 58, 59, 61, 62 and 63, and particularly preferred ones are Compounds Nos. 7, 18, 25, 26, 30 and 63.

The compound having the above formula (I) of the present invention can be prepared by, for example, Preparation method (A), (B), (C), (D) or (E) shown below.

Preparation method A

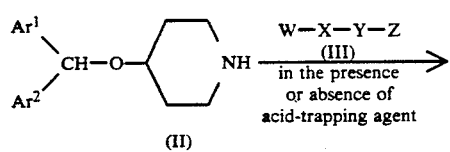

Preparation method B

The compound in which X is a group having

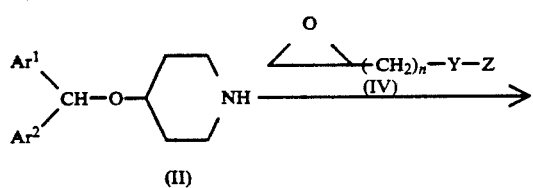

-continued $$\underset{Ar^2}{\overset{Ar^1}{>}}CH-O-\underset{}{\overset{}{\bigcirc}}N-CH_2\underset{OH}{\overset{}{C}}H(CH_2)_n-Y-Z \quad (I\text{-}1)$$

Preparation method C

The compound in which Y is —CONH— group

Preparation method C-1

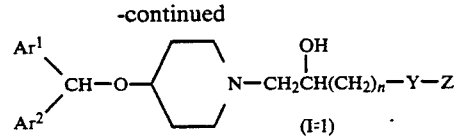

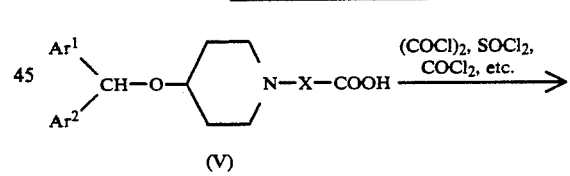

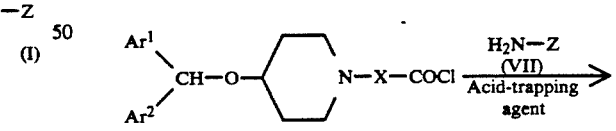

Preparation method C-2

-continued

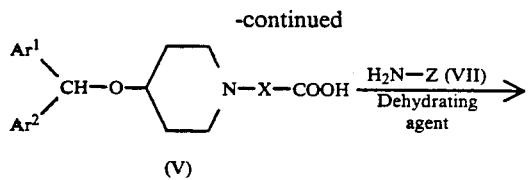

(V)

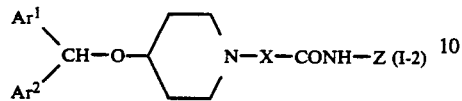

(I-2)

Preparation method D

The compound in which Z is a phenyl group substituted by —CONHR¹

Preparation method D-1

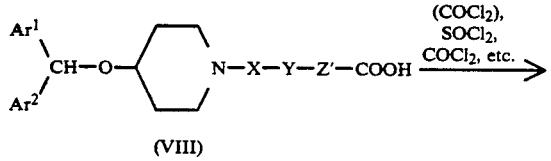

(VIII)

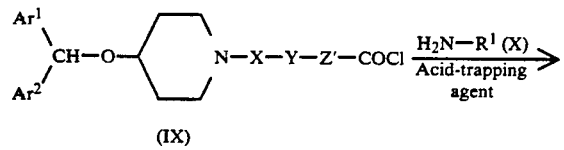

(IX)

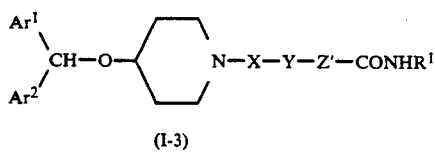

(I-3)

Preparation method D-2

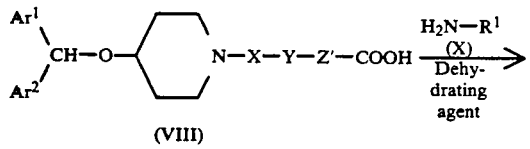

(VIII)

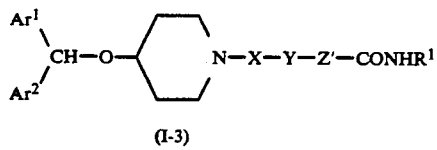

(I-3)

Preparation method E

The compound in which Z is a phenyl group substituted by tetrazolyl group or a group having

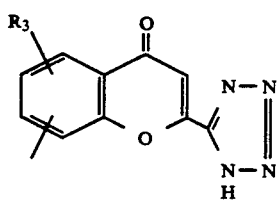

-continued

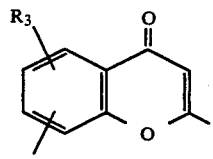

(XI)

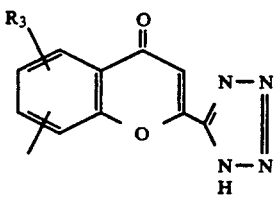

(I-4)

In the above reaction schemes, $Ar^1$, $Ar^2$, X, Y and Z each represent the same meanings as described above; W represents an eliminatable atom or group such as chlorine atom, bromine atom, iodine atom, methanesulfonyloxy group and p-toluenesulfonyloxy group; n represents an integer of 1 to 8; Z' represents a phenylene group or a phenylene group having a substituent other than —CONHR¹; $R^1$ and $R^3$ each represent the same meanings as described above; Z" represents a phenylene group having a substituent other than tetrazolyl group or a group having $$\text{[structure with } R_3, O\text{]}$$

As shown in the above reaction schemes, the compound (I) of the present invention can be prepared by reacting the compound (II) with the compound (III) in the presence or absence of an acid-trapping agent (Preparation method A), by reacting the compound (II) with the compound (IV) (Preparation method B), by reacting the acid chloride (VI) prepared from the compound (V) according to Preparation method A or Preparation method B with the compound (VII) (Preparation method C - 1) or by directly dehydrating and condensing the compound (V) and the compound (VII) (Preparation method C - 2).

The compound in which Z is a phenyl group substituted by —CONHR¹, a phenyl group substituted by tetrazolyl or a group having $$\text{[structure with } R_3, O, N-N, H\text{]}$$

can be also prepared by Preparation method D or Preparation method E, respectively.

In the preparation according to Preparation method A, as a solvent to be used, there may be mentioned an aprotic polar solvent such as dimethylsulfoxide, dimethylformamide, hexamethylphosphoric triamide and dimethylacetamide; an aromatic hydrocarbons such as benzene, toluene and xylene; halogenated hydrocarbons such as dichloromethane, dichloroethane, chloroform and carbon tetrachloride; ketones such as acetone and methyl ethyl ketone; ethers such as diethyl ether, tetrahydrofuran and dioxane; esters such as methyl acetate and ethyl acetate; alcohols such as methanol, ethanol, n-propanol, isopropanol and n-butanol; and nitriles such as acetonitrile. As the acid-trapping agent, there may be exemplified by tertiary amines such as 1,8-diazabicyclo[5.4.0]-7-undecene, 1,5-diazabicyclo[4.3.0]-5-nonene, triethylamine, tributylamine, pyridine, picoline, lutidine and collidine; a metal alkoxide such as sodium methoxide, sodium ethoxide, potassium-t-butoxide; and an inorganic base such as sodium carbonate and potassium carbonate. The amount of the acid-trapping agent to be used is preferably an equimolar amount to a 5-fold molar amount based on the compound (III), but when the tertiary amines are used as the above acid-trapping agent, they may be used as a solvent with a far excessive amount. Further, when the compound (II) is used with the 2-fold or more moles based on the compound (III), the reaction can proceed smoothly without adding any other acid-trapping agent since the excessive compound (II) acts as an acid-trapping agent.

In the preparation according to Preparation method B, there may be generally used the same solvents as in Preparation method A, but the reaction also proceeds in the absence of a solvent.

In the preparation according to Preparation method C or Preparation method D, as a solvent to be used, there may be mentioned an aprotic polar solvent such as dimethylsulfoxide, dimethylformamide, hexamethylphosphoric triamide and dimethylacetamide; ketones such as acetone and methyl ethyl ketone; ethers such as diethyl ether, tetrahydrofuran and dioxane; aromatic hydrocarbons such as benzene, toluene and xylene; esters such as methyl acetate and ethyl acetate; nitriles such as acetonitrile; and halogenated hydrocarbons such as dichloromethane, dichloroethane, chloroform and carbon tetrachloride. As a dehydrating agent, there may be used carbodiimides such as dicyclohexylcarbodiimide and 1-ethyl-3-(3-dimethylaminopropyl)carbodiimide, and the amount to be used is an equimolar amount to 5-fold molar amount based on the compounds (V) and (VIII).

In the preparation according to Preparation method C - 1 or D - 1, conversion of the compound (V) or (VIII) into the compound (VI) or (IX) can be carried out according to the conventional method by using oxalyl chloride, phosgene or thionyl chloride. The intermediate compound (VI) or (IX) may be isolated, or else, the compound (V) or (VIII) may be converted into the compound (vI) or (IX) by using an equimolar amount of oxalyl chloride, phosgene or thionyl chloride as described above, followed by addition of the compound (VII) or (X) without isolation. The reaction of the acid chloride (VI) or (IX) and the compound (VII) or (X) is carried out in the presence of an acid-trapping agent, and the kind of the acid-trapping agent is the same as described above in Preparation method A, and the amount to be used is an equimolar amount to a 5-fold molar amount based on the compounds (V) and (VIII).

The reactions in Preparation method A, B, C, D and E described above are each carried out at a temperature range of 0° to 200° C. The reaction time may vary depending on other conditions, but may be sufficient with generally 1 to 40 hours.

After completion of the reaction, the desired compound of the reaction can be obtained by processing a reaction mixture according to the conventional method, and further can be purified by using the conventional purification means such as a recrystallization method and column chromatography, if necessary. Further, the compound can be also made into a desired salt as described above according to the conventional method, if necessary.

In the compound having the formula (I) thus prepared, an optical isomer or a geometrical (cis and trans) isomer based on an asymmetric carbon atom in a molecule thereof may sometimes exist. In such a case, each stereoisomer of the compound (I) can be obtained by carrying out the above reaction using the corresponding optically separated starting material (e.g. the compounds (II), (III), (IV), (V), (VII), (VIII), (X) and (XI)), or by processing a mixture of optical isomers or geometrical isomers of the compound (I) according to the conventional optical resolution method or separation method.

The compound (II) which is a starting material of the above preparation methods can be obtained easily by, for example, the method disclosed in Japanese Provisional Patent Publication No. 25465/1990.

The desired compounds of the present invention having the above formula (I) and salts thereof show significant antihistaminic action and antileukotrienic action in the pharmacological test described below.

Test method

Ileum samples removed from guinea pigs were suspended isotonically in a Magnus tank containing a 95% $O_2$ and 5% $CO_2$ saturated Tyrode solution to determine inhibitory effect of the test compounds ($10^{-7}$ M) on the ileum shrinkage induced by histamine ($10^{-5}$ M) or leukotoriene ($10^{-8}$ M). The inhibitory ratio (%) was determined by the following formula.

Inhibition ratio (%) =

$$\left[ 1 - \frac{\text{Shrinkage induced by histamine } (10^{-5} M) \text{ or leukotoriene } (10^{-8} M) \text{ in the presence of the test compound } (10^{-7} M)}{\text{Shrinkage induced by histamine } (10^{-5} M) \text{ or leukotoriene } (10^{-8} M)} \right] \times 100$$

Test results

The test results are shown in Table 2.

TABLE 2

|  | Inhibition ratio against shrinkage by histamine (%) | Inhibition ratio against shrinkage by leukotoriene (%) |
| --- | --- | --- |
| Compound in Example 2 | 96 | 30 |
| Compound in Example 7 | 67 | 51 |
| Compound in Example 14 | 69 | 39 |
| Compound in Example 38 | 32 | 33 |
| Compound in Example 41 | 31 | 31 |
| Compound in Example 44 | 43 | 35 |
| Compound in Example 45 | 40 | 30 |
| Compound in Example 47 | 38 | 36 |
| Compound in | 58 | 37 |

TABLE 2-continued

| | Inhibition ratio against shrinkage by histamine (%) | Inhibition ratio against shrinkage by leukotoriene (%) |
|---|---|---|
| Example 60 | | |

Thus, the compounds (I) of the present invention and salt thereof are useful for treatment of allergic skin diseases such as urticaria, eczema and dermatitis, sternutatio, pituita and cough caused by upper respiratory inflammation such as allergic rhinitis and cold, and bronchial asthma in human beings and animals. As administration form for such a purpose, there may be mentioned, for example, oral administration using a tablet, a capsule, a granule, a powder and a syrup and parenteral administration using an intravenous injection, an intramuscular injection, a suppository, an inhalant, a percutaneous absorbent, a collyrium and a collunarium.

The dose varies depending on age, body weight, symptom, administration form and administration time, but the compound is generally administered to an adult orally or parenterally at a dose of about 1 to 50 mg per day at one time or devided into several times.

EXAMPLES

The present invention is described in detail by referring to Examples.

EXAMPLES 1

Synthesis of 1-[3-(4-acetyl-3-hydroxy-2-n-propylphenoxy)propyl]-4-[(4-chlorophenyl-2-pyridylmethoxyl]piperidine. fumarate

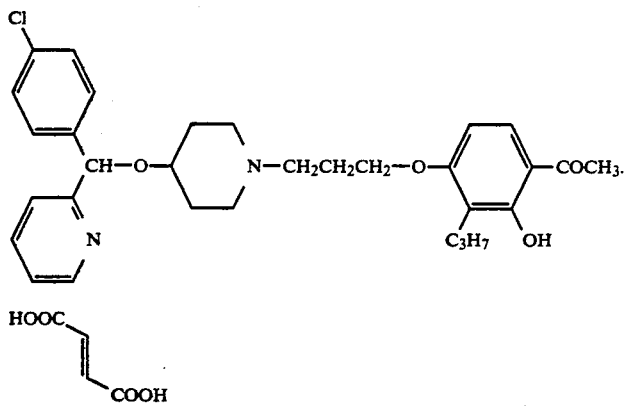

a) 1.94 g (10.0 mmol) of 2,4-dihydroxy-3-n-propylacetophenone and 2.62 g (13.0 mmol) of 1,3-dibromopropane were heated and stirred at 70° C. for 3 hours in a solution of 0.8 g (20.0 mmol) of sodium hydroxide and 6 ml of water in the presence of 0.34 g (1.5 mmol) of triethylbenzylammonium chloride. After completion of the reaction, water was added and the reaction mixture was extracted with chloroform, and then the organic layer was concentrated under reduced pressure. The residue was applied to silica gel column chromatography using a solvent mixture of hexane and ethyl acetate in a volume ratio of 5:1 as an eluent to obtain 1.04 g (yield: 33%) of 4-(3-bromopropoxy)-2-hydroxy-3-n-propylacetophenone as brown crystals.

MS spectrum (EI)m/e: 314 (M+).
(CI)m/e: 315 (M+ +1).
$^1$H-NMR spectrum (CDCl$_3$, $\delta$):
0.95 (3 H, t), 1.44–1.62 (2 H, m), 2.38 (2 H, m), 2.52–2.69 (5 H, s, m), 3.62 (2 H, t), 4.19 (2 H, t), 6.44 (1 H, d), 7.59 (1 H, d), 12.74 (1 H, s)

b) In 6 ml of acetone were dissolved 0.80 g (2.64 mmol) of 4-[(4-chlorophenyl)-2-pyridylmethoxy]piperidine and 0.95 g (3.01 mmol) of 4-(3-bromopropoxy)-2-hydroxy-3-n-propylacetophenone. To the mixed solution was added 0.44 g (3.18 mmol) of potassium carbonate, and the mixture was heated and stirred at an oil bath temperature of at around 60° C. for 6.5 hours. After completion of the reaction, insolubles were removed by filtration, and the filtrate was concentrated under reduced pressure. The residue was applied to silica gel column chromatography using a solvent mixture of chloroform and methanol in a volume ratio of 20:1 as an eluent to obtain 1.24 g (yield: 87%) of 1-[(4-acetyl-3-hydroxy-2-n-propylphenoxy)propyl]-4-[(4-chlorophenyl)-2-pyridylmethoxy]piperidine as a slightly brown oily product.

MS spectrum (EI)m/e: no M+ peak.
(CI)m/e: 537 (M+ +1).
$^1$H-NMR spectrum (CDCl$_3$, $\delta$):
0.93 (3 H, t), 1.51 (2 H, m), 1.65–2.10 (7 H, b), 2.30–2.68 (6 H, s, m), 2.71–2.86 (2 H, b), 3.49 (1 H, m), 4.08 (2 H, t), 5.61 (1 H, s), 6.43 (2 H, d), 7.12–7.19 (1 H, m), 7.25–7.75 (8 H, m), 8.52 (1 H, d)

c) In 20 ml of ethanol were dissolved 1.14 g (2.12 mmol) of the oily product obtained in the above b) and 0.25 g (2.15 mmol) of fumaric acid to give a homogeneous solution.

The resulting mixed solution was concentrated under reduced pressure, and isopropyl ether was added to the residue to crystallize. The filtered product was recrystallized from ethyl acetate to obtain 0.66 g (yield: 47%) of 1-[3-(4-acetyl-3-hydroxy-2-n-propylphenoxy)-propyl]-4-[(4-chlorophenyl-2-pyridylmethoxy]-piperidine.furamate as colorless crystals.

Melting point: 156.5° to 157.5° C.
Elemental analysis:
In terms of $C_{31}H_{37}ClN_2O_4 \cdot C_4H_4O_4 \cdot \frac{1}{2}H_2O$,
Calculated value (%): C 63.92; H 6.36; N 4.26.
Found value (%): C 63.99; H 6.27; N 4.11.

EXAMPLES 2 to 43

The following compounds were synthesized according to the method in Example 1.

TABLE 3

$$\text{Ar}^1\text{-CH(Ar}^2\text{)-O-CH(cyclohexyl)-N-X-Y-Z}$$

Structure: Ar¹ and Ar² attached to CH, which connects via O to a 4-piperidinyl group (N—X—Y—Z).

| Example | Ar¹ | Ar² | X | Y | Z | Property (m.p.) | NMR spectrum (CDCl₃, δ) |
|---|---|---|---|---|---|---|---|
| 2 | phenyl | phenyl | $(CH_2)_3$ | O | 3-OCH₃, 4-COCH₃ phenyl | Pale orange amber viscous product | 1.77(2H, b), 1.92(2H, b), 2.07(2H, t), 2.51(2H, b), 2.58(3H, s), 2.78(2H, b), 3.47(1H, m), 3.89(3H, s), 4.15(2H, t), 5.51(1H, s), 6.90(1H, d), 7.20~7.38 ((10H, m), 7.51~7.58(2H, m) |
| 3 | phenyl | phenyl | $(CH_2)_3$ | O | 3-OCH₃, 4-COOCH₃ phenyl | Orange amber viscous product | 1.84(2H, b), 2.03(2H, b), 2.13(2H, b), 2.41(2H, b), 2.65(2H, b), 2.87(2H, b), 3.55(1H, m), 3.89(3H, s), 3.90(3H, s), 4.14(2H, t), 5.62(1H, s), 6.90(1H, d), 7.11~7.72((11H, m), 8.51(1H, m) |
| 4 | phenyl | phenyl | $(CH_2)_3$ | O | 2-OH, 4-COOCH₃ phenyl | Colorless crystal mp. 91.5~93.0° C. | 1.68~2.08(6H, m), 2.18(2H, b), 2.49(2H, t), 2.76(2H, b), 3.47(1H, m), 4.08(2H, t), 5.55(1H, s), 6.35(1H, d), 6.48(1H, d), 6.64(1H, s), 7.20~7.39 (10H, m), 7.52(3H, m), 7.96(2H, m), 12.70(1H, b) |
| 5 | phenyl | phenyl | $(CH_2)_3$ | O | flavone derivative (2-phenyl-chromone with OH) | Yellowish foamy product | |
| 6 | phenyl | phenyl | $(CH_2)_3$ | O | 3,5-di-OCH₃, 4-COCH₃ phenyl | Pale Yellowish foamy product | 2.01(2H, b), 2.28(4H, b), 2.58(3H, s), 3.02~3.20(6H, m), 3.25(1H, m), 3.87(3H, s), 3.88(3H, s), 4.10(2H, t), 5.48(1H, s), 7.20(2H, s, s), 7.22~7.35(10H, m) |

TABLE 3-continued

Structure: Ar¹Ar²CH—O—[cyclohexyl]—N—X—Y—Z

| Example | Ar¹ | Ar² | X | Y | Z | Property (m.p.) | NMR spectrum (CDCl₃, δ) |
|---|---|---|---|---|---|---|---|
| 7 | phenyl | phenyl | ‑(CH₂)₇‑ | O | (2H-chromen-2-one with CH₃ and CH₂CH=CH₂ substituents) | Orange crystal mp. 95~97° C. | |
| 8 | phenyl | phenyl | ‑(CH₂)₇‑ | O | (6-methoxy-2H-chromen-2-one) | Pale yellowish foamy product | 1.91(2H, b), 2.05~2.33(4H, m), 2.15~3.03(6H, m), 3.62(1H, m), 3.87(3H, s), 4.15(2H, t), 5.49(1H, s), 6.28(1H, d), 6.82(2H, d), 7.23~7.37(10H, m), 7.60(1H, m) |
| 9 | phenyl | phenyl | ‑(CH₂)₇‑ | O | (benzene with COOH, OCH₃) | Orange foamy product | 1.95(2H, b), 2.16(4H, b), 3.01(6H, b), 3.69(1H, m), 3.86(3H, s), 4.19(2H, t), 5.48(1H, s), 6.69(1H, d), 7.19~7.37(11H, m), 7.48(1H, d), 8.71((1H, b) |
| 10 | phenyl | phenyl | ‑(CH₂)₇‑ | O | (benzene with CN, CH₃) | Orange oily product | 1.68~2.02(6H, m), 2.17(2H, b), 2.47(2H, t), 2.76(2H, b),3.45(1H, m), 4.04(2H, t), 5.52(1H, s), 6.92(2H, m), 7.21~7.37 (10H, m), 7.56(2H, m), |
| 11 | phenyl | phenyl | ‑(CH₂)₇‑ | O | (benzene with COOCH₃, OH, CH₂CH=CH₂, CH₃) | Orange oily product | 1.60~2.00(6H, m) 2.16(2H, b), 2.49(2H, t), 2.75(2H, b), 3.40(2H, d), 3.49(1H, m), 3.89(3H, s), 4.06(2H, t), 4.99(2H, m), 5.51(1H, s), 5.92(1H, m), 6.42(1H, d), 7.20~7.39(10H, m), 7.69(1H, d), 11.09(1H, s) |

TABLE 3-continued
| Example | Ar¹ | Ar² | X | Y | Z | Property (m.p.) | NMR spectrum (CDCl₃, δ) |
|---|---|---|---|---|---|---|---|
| 12 | 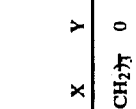 |  | ƒCH₂)₇ | O |  | Orange oily product | 1.40(3H, t), 1.67~2.06(6H, m), 2.15(2H, b), 2.49(2H, t), 2.74(2H, b), 3.47(1H, m), 4.10(2H, t), 4.40(2H, q), 5.51(1H, s), 6.80~6.91(2H, m), 7.19~7.38(10H, m), 7.49(1H, m), 8.49(1H, s) |
| 13 |  |  | ƒCH₂)₇ | O | 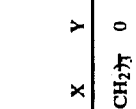 | Colorless crystal mp. 88~90° C. | |
| 14 |  | 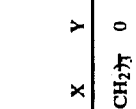 | ƒCH₂)₇ | O |  | Pale yellow crystal mp. 90~91° C. | |
| 15 | 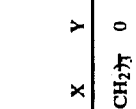 |  | ƒCH₂)₇ | O |  | Orange amber viscous product | 1.69~1.97(6H, m), 2.17(2H, b), 2.45(2H, t), 2.75(2H, b), 3.45(1H, m), 3.91(3H, s), 4.21(2H, t), 5.51(1H, s), 6.25(1H, d), 6.89(1H, d), 7.21~7.37(10H, m), 7.60(1H, d), 8.01(1H, s) |
| 16 |  |  | ƒCH₂)₇ | O | 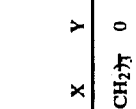 | Pale brownish crystal mp. >250° C. | |

TABLE 3-continued $$Ar^1\!\!-\!\!\underset{Ar^2}{\overset{}{CH}}\!\!-\!\!O\!\!-\!\!\bigcirc\!\!-\!\!N\!\!-\!\!X\!\!-\!\!Y\!\!-\!\!Z$$

| Example | Ar$^1$ | Ar$^2$ | X | Y | Z | Property (m.p.) | NMR spectrum (CDCl$_3$, δ) |
|---|---|---|---|---|---|---|---|
| 17 | 4-F-C$_6$H$_4$ | 4-F-C$_6$H$_4$ | ‒(CH$_2$)$_3$‒ | O | 2-OCH$_3$, 4-COCH$_3$-C$_6$H$_3$ | Pale orange oily product | 1.73(2H, b), 1.88(2H, b), 2.04(2H, t), 2.19(2H, b), 2.53(2H, m), 2.57(3H, s), 2.78(2H, b), 3.42(2H, b), 3.91(3H, s), 4.15(2H, t), 5.49(1H, s), 6.89~7.07(5H, m), 7.24~7.32(4H, m), 7.50~7.59(2H, m) |
| 18 | 4-F-C$_6$H$_4$ | 4-F-C$_6$H$_4$ | ‒(CH$_2$)$_3$‒ | O | 4-COOCH$_3$-C$_6$H$_4$ | Colorless crystal mp. 68~70° C. | |
| 19 | 4-F-C$_6$H$_4$ | 4-F-C$_6$H$_4$ | ‒(CH$_2$)$_3$‒ | O | 4-COOH-C$_6$H$_4$ | Colorless foamy product | 1.91(2H, b), 2.19(4H, b), 2.99(6H, b), 3.62(1H, m), 4.09(2H, t), 5.43(1H, s), 6.68~6.77(2H, m), 6.95~7.05(4H, m), 7.20~7.31(4H, m)9.60(1H, b) |
| 20 | 4-F-C$_6$H$_4$ | 4-F-C$_6$H$_4$ | ‒(CH$_2$)$_3$‒ | O | 4-CN-C$_6$H$_4$ | Orange oily product | 1.66~2.01(6H, b), 2.14(2H, b), 2.49(2H, t), 2.74(2H, b), 3.40(1H, m), 4.03(2H, t), 5.47(1H, s), 6.91~7.05(5H, m), 7.21~7.31(4H, m), 7.51~7.58(2H, m), 8.01 (1H, m) |
| 21 | 4-F-C$_6$H$_4$ | 4-F-C$_6$H$_4$ | ‒(CH$_2$)$_3$‒ | O | 4-C(CH$_3$)$_3$-C$_6$H$_4$ | Pale yellowish crystal mp. 84~85° C. | |
| 22 | 4-Cl-C$_6$H$_4$ | 2-pyridyl | ‒(CH$_2$)$_3$‒ | O | 2-OCH$_3$-C$_6$H$_4$ | Pale yellowish amber viscous product | 1.77(2H, b), 1.89(2H, b), 2.30(2H, b), 2.80~2.99(4H, m), 3.49(1H, m), 3.86(3H, s), 4.14(2H, t), 5.61(1H, s), 6.91(3H, m), 7.15(1H, m), 7.23~7.72(6H, m), 8.51(1H, m) |

TABLE 3-continued $$\text{Ar}^1\text{Ar}^2\text{CH-O-}\bigcirc\text{-N-X-Y-Z}$$

| Example | Ar¹ | Ar² | X | Y | Z | Property (m.p.) | NMR spectrum (CDCl₃, δ) |
|---|---|---|---|---|---|---|---|
| 23 | 4-Cl-C₆H₄ | 2-pyridyl | ₊(CH₂)₃₊ | O | 4-I-C₆H₄ | Yellowish amber viscous product | 1.80(2H, b), 1.91(2H, b), 2.35(2H, b), 2.82(4H, m), 3.49(1H, m), 4.07(2H, t), 5.60(1H, s), 6.67(2H, m), 7.11~7.72(9H, m), 8.51(1H, m) |
| 24 | 4-Cl-C₆H₄ | 2-pyridyl | ₊(CH₂)₃₊ | O | 4-OCH₃-C₆H₄ | Orange oily product | 1.85(2H, b), 1.98(2H, b), 2.49(2H, b), 2.82~3.05(4H, m), 3.55(1H, m), 3.77(3H, s), 4.12(2H, t), 5.59(1H, s), 6.83(4H, s), 7.12~7.72(7H, m), 8.51(1H, m) |
| 25 | 4-Cl-C₆H₄ | 2-pyridyl | ₊(CH₂)₃₊ | O | 3-OCH₃-C₆H₄ | Yellowish oily product | 1.76(2H, b), 1.88(2H, b), 2.29(2H, b), 2.78(2H, t), 2.82(2H, b), 3.48(1H, m), 3.78(3H, s), 4.07(2H, t), 5.60(1H, s), 6.48~6.43(3H, m), 7.11~7.71(8H, m), 8.49(1H, m) |
| 26 | 4-Cl-C₆H₄ | 2-pyridyl | ₊(CH₂)₃₊ | O | 2,5-(CH₃)₂-C₆H₃ | Dark orange oily product | 1.76(2H, b), 1.90(2H, b), 2.15(3H, s), 2.25(3H, s), 2.36(2H, b), 2.82(2H, t), 2.90(2H, b), 3.49(1H, m), 4.06(2H, t), 5.60(1H, s), 6.18(1H, d), 6.94(2H, m) 7.10~7.71(7H, m), 8.50(1H, m) |
| 27 | 4-Cl-C₆H₄ | 2-pyridyl | ₊(CH₂)₃₊ | O | 4-Cl-C₆H₄ | Pale orange oily product | 1.78(2H, b), 1.91(2H, b), 2.30(2H, b), 2.79(2H, t), 2.87(2H, b), 3.49(1H, m), 4.05(2H, t), 5.60(1H, s), 6.79~6.85(2H, m), 7.14~7.73(9H, m), 8.51(1H, m) |
| 28 | 4-Cl-C₆H₄ | 2-pyridyl | ₊(CH₂)₃₊ | O | 3,4-methylenedioxyphenyl | Colorless crystal mp. 143~145° C. | |

TABLE 3-continued

| Example | Ar¹ | Ar² | X | Y | Z | Property (m.p.) | NMR spectrum (CDCl₃, δ) |
|---|---|---|---|---|---|---|---|
| 29 | 4-Cl-C₆H₄ | 2-pyridyl | (CH₂)₃ | O | 3,5-dimethoxyphenyl | Yellowish oily product | 1.75(2H, b), 1.87(2H, b), 2.28(2H, b), 2.75(2H, t), 2.85(2H, b), 3.49(1H, m), 3.74(6H, s), 4.03(2H, t), 5.11(1H, s), 6.08(3H, s), 7.08~7.70(7H, m), 8.49(1H, m) |
| 30 | 4-Cl-C₆H₄ | 2-pyridyl | (CH₂)₃ | O | 4-cyanophenyl | Orange oily product | 1.76(2H, b), 1.87(2H, b), 2.30(2H, b), 2.80(2H, t), 2.85(2H, b), 3.49(1H, m), 4.13(2H, t), 5.71(1H, s), 6.89~6.99(2H, m), 7.11~7.72(9H, m), 8.51(1H, m) |
| 31 | 4-Cl-C₆H₄ | 2-pyridyl | (CH₂)₃ | O | 4-acetylphenyl | Orange amber viscous product | 1.78(2H, b), 1.92(2H, b), 2.34(2H, b), 2.57(3H, s), 2.82(2H, t), 2.87(2H, b), 3.51(1H, m), 4.18(2H, t), 5.62(1H, s), 6.90~6.97 (2H, m), 7.12~7.72(7H, m), 7.91~7.97(2H, m), 8.51(1H, m) |
| 32 | 4-Cl-C₆H₄ | 2-pyridyl | (CH₂)₃ | O | 3-chlorophenyl | Orange oily product | 1.75(2H, b), 1.88(2H, b), 2.28(2H, b), 2.74(2H, t), 2.83(2H, b), 3.49(1H, m), 4.05(2H, t), 5.61(1H, s), 6.78(1H, m), 6.88~6.95 (2H, m), 7.09~7.71(8H, m), 8.51(1H, m) |
| 33 | 4-Cl-C₆H₄ | 2-pyridyl | (CH₂)₃ | O | chromone-2-carboxylic acid, 8-propyl | Colorless crystal m.p. >250° C. | |

TABLE 3-continued $$\begin{array}{c} Ar^1 \\ | \\ CH-O-\underset{\text{piperidine}}{\bigcirc}-N-X-Y-Z \\ | \\ Ar^2 \end{array}$$

| Example | Ar¹ | Ar² | X | Y | Z | Property (m.p.) | NMR spectrum (CDCl₃, δ) |
|---|---|---|---|---|---|---|---|
| 34 | 4-Cl-C₆H₄ | 2-pyridyl | ⁻(CH₂)₇⁻ | O | 3-COCH₃-2-OH-5-CH₃-6-CH₂CH₂CH₃-phenyl | Yellowish oily product | 0.94(3H, t), 1.52(2H, q), 1.75(2H, b), 1.89(2H, b), 2.33(2H, b), 2.58(3H, s), 2.61(2H, t), 7.78~2.94(4H, m), 3.50(1H, m), 4.15(2H, t), 5.61(1H, s), 6.41(1H, d), 7.11~7.71(8H, m), 8.51(1H, m), 12.73(1H, s) |
| 35 | 4-Cl-C₆H₄ | 2-pyridyl | ⁻(CH₂)₇⁻ | O | 3-COCH₃-2-OH-5-CH₃-6-CH₂CH₂CH₃-phenyl | Orange oily product | 0.94(3H, t), 1.45~1.61(6H, m), 1.69~1.95(8H, m), 2.14(2H, b), 2.35(2H, b), 2.59(3H, s), 2.60~2.85(4H, m), 3.49(1H, m), 4.01(2H, t), 5.61(1H, s), 6.40(1H, d), 7.11~7.72(8H, m), 8.50(1H, m), 12.73(1H, s) |
| 36 | 4-Cl-C₆H₄ | 2-pyridyl | ⁻(CH₂)₇⁻ | O | 3-COCH₃-2-OH-5-CH₃-6-CH₂CH₂CH₃-phenyl | Brownish oily product | 0.94(3H, t), 1.31~1.63(8H, m), 1.70~2.00(6H, m), 2.15(2H, b), 2.34(2H, b), 2.56(3H, s), 2.60~2.81(4H, m), 3.48(1H, m), 4.02(2H, t), 5.61(1H, s), 6.41(1H, d), 7.11~7.72(8H, m), 8.51(1H, m), 12.74(1H, s) |
| 37 | 4-Cl-C₆H₄ | 2-pyridyl | ⁻(CH₂)₇⁻ | O | 3-COCH₃-2-OH-5-CH₃-6-CH₂CH₂CH₃-phenyl | Yellowish oily product | 0.94(3H, t), 1.29~1.61(16H, m), 1.65~1.99(6H, m), 2.10(2H, b), 2.26(2H, b), 2.58(3H, s), 2.64(2H, t), 2.73(2H, b), 3.47(1H, m), 4.01(2H, t), 5.61(1H, s), 6.41(1H, d), 7.11~7.71(8H, m), 8.51(1H, m), 12.73(1H, s) |

TABLE 3-continued

| Example | Ar¹ | Ar² | X | Y | Z | Property (m.p.) | NMR spectrum (CDCl₃, δ) |
|---|---|---|---|---|---|---|---|
| 38 | 4-Cl-C₆H₄ | 2-pyridyl | ₊CH₂₎₃ | O | 3-COCH₃, 2-OH, 6-CH₃, (CH₂CH=CH₂) phenyl | Pale yellowish oily product | 1.64~1.80(4H, m), 1.85~2.01(4H, m), 2.16(2H, b), 2.57(3H, s), 2.75(2H, b), 3.39(2H, d), 3.48(1H, m), 4.09(2H, t), 4.99(2H, m), 5.60(1H, s), 5.90(1H, m), 6.45(1H, d), 7.12~7.72(8H, m), 8.51(1H, m), 12.76(1H, s) |
| 39 | 4-Cl-C₆H₄ | 2-pyridyl | ₊CH₂₎₃ | O | 4-COCH₃, 3-OCH₃, phenyl | Pale yellowish foamy product | 1.87(2H, b), 2.04~2.30(6H, m), 2.58(3H, s), 2.71(2H, b), 2.91(2H, b), 3.60(1H, m), 3.92(3H, s), 4.17(2H, t), 5.60(1H, s), 6.90(1H, d), 7.12~7.71(9H, m), 8.51(1H, m) |
| 40 | 4-Cl-C₆H₄ | 2-pyridyl | ₊CH₂₎₃ | O | 4-COOCH₃, phenyl | Dark orange oily product | 1.86(2H, b), 2.01~2.20(4H, m), 2.51(2H, b), 2.69(2H, b), 2.90(2H, b), 3.60(1H, m), 3.90(3H, s), 4.07(2H, t), 5.60(1H, s), 6.85(2H, d), 6.91(2H, d), 7.12~7.74(7H, m), 7.94(2H, d), 7.99(2H, d), 8.51(1H, m) |
| 41 | phenyl | phenyl | ₊CH₂₎₃ | O | chromone with COO(CH₂)₃CH₃, CH₂CH=CH₂, CH₃ substituents | Colorless crystal mp. 188~190° C. | |

TABLE 3-continued

| Example | Ar¹ | Ar² | X | Y | Z | Property (m.p.) | NMR spectrum (CDCl₃, δ) |
|---|---|---|---|---|---|---|---|
| 42 | Ph | Ph | (CH₂)₃ | O | chromone with CONH₂, CH₂CH=CH₂, CH₃ | Pale yellowish prism-like crystal mp. 174~175° C. | |
| 43 | Ph | Ph | (CH₂)₃ | O | chromone with CN, CH₂CH=CH₂, CH₃ | Orange crystal mp. 135~137° C. | |

Example 44

Synthesis of 1-{(3-(4-acetyl-3-hydroxy-2-n-propylphenoxy)-2-hydroxy]propyl}-4-[bis(4-fluorophenyl)methoxy]-piperidine fumarate

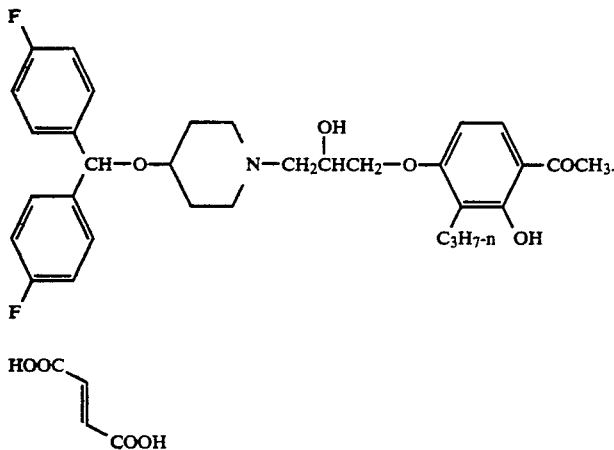

a) To 0.88 g (2.89 mmol) of 4-[bis(4-fluorophenyl)methoxy]piperidine dissolved in 10 ml of benzene and 5 ml of dimethylformamide was added 0.94 g (3.76 mmol) of 4-(2,3-epoxy)propoxy-2-hydroxy-3-n-propylacetophenone synthesized by referring to Journal of Medicinal Chemistry, vol. 20, pp. 371 to 379 (1977), and the mixture was refluxed for 4 hours. After completion of the reaction, the concentrated residue under reduced pressure was applied to silica gel column chromatography using a solvent mixture of chloroform and methanol in a volume ratio of 30:1 as an eluent to obtain 1.25 g (yield: 78%) of 1-{([3-(4-acetyl-3-hydroxy-2-n-propylphenoxy)-2-hydroxy]propyl}-4-[bis(4-fluorophenyl)methoxy]piperidine as a slightly orange oily product.

MS spectrum (EI)m/e: no M+ peak.
(CI)m/e: 554 (M++1).

$^1$H-NMR spectrum (CDCl$_3$, δ): 0.93 (3 H, t), 1.46–1.60 (2 H, m), 1.68–2.29 (6 H, b), 2.35–2.79 (9 H, s, m), 3.47 (1 H, m), 4.05 (3 H, m), 5.49 (1 H, s), 6.44 (2 H, d), 6.95–7.09 (4H, m), 7.21–7.35 (4H, m), 7.58 (1 H, d).

b) 1.10 g (1.98 mmol) of the oily product obtained in the above a) was dissolved in 10 ml of ethanol and 0.23 g (1.98 mmol) of fumaric acid was added, and the mixture was heated to give a homogeneous solution. The solution was allowed to stand overnight and then concentrated under reduced pressure to obtain crude crystals. The crystals were recrystallized from 190 ml of ethanol to obtain 0.79 g (yield: 64%) of 1-{([3-(4-acetyl-3-hydroxy-2-n-propylphenoxy)-2-hydroxy]propyl)-4-[bis(4-fluorophenyl)methyoxy]piperidine.fumarate as colorless crystals.

Melting point: 191.0° to 192.5° C.
Elemental analysis:
In terms of C$_{34}$H$_{39}$NO$_7$F$_2$·½H$_2$O,
Calculated value (%): C 65.79; H 6.50; N 2.26.
Found value (%): C 65.95; H 6.47; N 2.37.

EXAMPLES 45 to 47

The following compounds were synthesized according to the method in Example 44.

TABLE 4

Ar$^1$\
    CH—O—[piperidine]—N—X—Y—Z\
Ar$^2$/

| Example | Ar$^1$ | Ar$^2$ | X | Y | Z | Property (m.p.) | NMR spectrum (CDCl$_3$, δ) |
|---|---|---|---|---|---|---|---|
| 45 | Cl—C$_6$H$_4$— | 2-pyridyl | —CH$_2$CH(OH)CH$_2$— | —O— | 4-acetyl-3-hydroxy-2-n-propylphenyl | Colorless crystal m.p. 177.5~179.0° C. | |

TABLE 4-continued

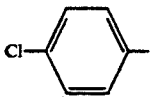

| Example | Ar¹ | Ar² | X | Y | Z | Property (m.p.) | NMR spectrum (CDCl₃, δ) |
|---|---|---|---|---|---|---|---|
| 46 | Cl-C₆H₄- | 2-pyridyl | -CH₂CH(OH)CH₂- | -O- | 2-COCH₃, phenyl-OH (ortho) | Orange oily product | 1.75(2H, b), 1.90(2H, b), 2.20(1H, m), 2.36~2.51(3H, m), 2.57(3H, s), 2.70(2H, b), 2.92(1H, b), 3.51(1H, m), 3.98~4.15(3H, m), 5.61(1H, s), 6.40~6.51(2H, m), 7.12~7.73(8H, m), 8.51(1H, m), 12.70(1H, b) |
| 47 | Cl-C₆H₄- | 2-pyridyl | -CH₂CH(OH)CH₂- | -O- | phenyl with COCH₃, OH, CH₂CH=CH₂ | Pale yellowish amber viscous product | 1.76(2H, b), 1.91(2H, b), 2.25(1H, m), 2.45(2H, b), 2.58(3H, s), 2.75(1H, m), 2.91(2H, m), 3.41(2H, d), 3.51(1H, m), 4.01~4.14(3H, m), 5.00(2H, m), 5.60(1H, s), 5.95(1H, m), 6.47(1H, d), 7.12~7.72(8H, m), 8.51(1H, m), 12.78(1H, b) |

Remarks: Example 45; ¼ fumarate

EXAMPLE 48

Synthesis of 1-{(3-{N-(3-acetyl-2-hydroxy-5-methyl)phenyl]car-bamoyl}propyl}-4-[(4-chlorophenyl)-2-pyridylmethoxy]piperidine

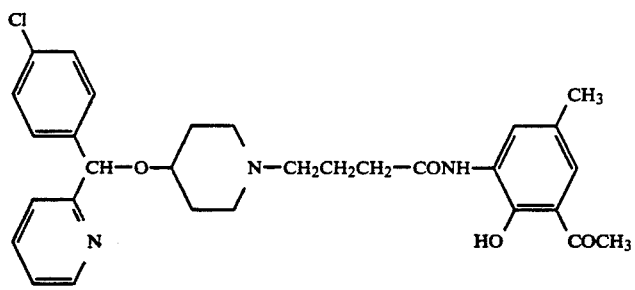

a) To 5.0 g (33.3 mmol) of 2-hydroxy-5-methylalacetophenone dissolved in 25 ml of acetic acid was added dropwise 5.3 ml of conc. nitric acid over about 30 minutes under cooling to around 15° C. and stirring. About 10 minutes after completion of the dropwise addition, the temperature of the reaction mixture rose to 35° C., and yellow crystals were precipitated. The reaction mixture was poured into ice water, and the crystals were filtered off and washed with about 300 ml of ice water. About 7 g of the obtained crude crystals were recrystallized from 70 ml of n-propanol to obtain 4.66 g (yield: 72%) of 2-hydroxy-5-methyl-3-nitroacetophenone as yellow needle crystals.

Melting point: 130° to 132° C.

MS spectrum (EI)m/e: 195 (M+).
(CI)m/e: 196 (M++1).
Elemental analysis:
In terms of C₉H₉NO₄,
Calculated value (%): C 55.39; H 4.65; N 7.18.
Found value (%): C 55.42; H 4.92; N 7.19.

b) In 200 ml of ethanol was dissolved 4.0 g (20.5 mmol) of 2-hydroxy-5-methyl-3-nitroacetophenone, and the mixture was stirred at room temperature for about 2 hours in the presence of 1.0 g of 5% palladium carbon while bubbling hydrogen gas thereinto. The inorganic substance was filtered off, and the filtrate was concentrated to obtain 3.30 g (yield: 97%) of 3-amino-2-hydroxy-5-methylacetophenone as brown needle crystals.

Melting point: 53° to 55° C.
MS spectrum (EI)m/e: 165 (M+).
(CI)m/e: 166 (M++1).
¹H-NMR spectrum (CDCl₃, δ):
2.24 (3 H, s), 2.59 (3 H, s), 3.85 (2 H, b), 6.78 (1 H, d), 6.95 (1 H, d), 12.28 (1 H, b).

c) To 1.0 g (2.57 mmol) of 4-(4-[(4-chlorophenyl)-2-pyridylmethoxy]piperidinyl)butanoic acid dissolved in 10 ml of dichloromethane was added 0.73 g (3.53 mmol) of dicyclohexylcarbodiimide, and the mixture was stirred at 0° C. for one hour. To the reaction mixture was added 0.47 g (2.85 mmol) of 3-amino-2-hydroxy-5-methylacetophenone, and the mixture was further stirred at 0° C. for 2 hours. The reaction mixture was allowed to stand at room temperature overnight and then concentrated under reduced pressure. To the residue was added ethyl acetate, and the insolubles were filtered off. The filtrate was concentrated under reduced pressure, and the residue was applied to silica gel column chromatography using a mixed solvent of chloroform and methanol in a volume ratio of 30:1 as an eluent to obtain 0.43 g (yield: 31%) of 1-{(3-{N-[(3-acetyl-2-hydroxy-5-methyl)phenyl]carbamoyl}propyl}-4-[(4-chlorophenyl)-2-pyridylmethoxy]piperidine as an orange foamy product.

MS spectrum (EI)m/e: no (M$^+$) peak.

(CI)m/e: 536 (M$^+$+1).

$^1$H-NMR spectrum (CDCl$_3$, δ): 1.67–2.02 (6 H, m), 2.12–2.25 (2 H, m), 2.34 (3 H, s), 2.76 (2 H, b), 3.49 (1 H, m), 5.59 (1 H, s), 7.11–7.71 (8 H, m), 8.18 (1 H, b), 8.43–8.52 (2 H, m), 12.66 (1 H, b).

EXAMPLES 49 to 58

The following compounds were synthesized according to the method in Example 48.

TABLE 5

Structure:
Ar¹–CH(Ar²)–O–[piperidine]–N–X–Y–Z

| Example | Ar¹ | Ar² | X | Y | Z | Property (m.p.) | NMR spectrum (CDCl₃, δ) |
|---|---|---|---|---|---|---|---|
| 49 | 4-F-C₆H₄ | 4-F-C₆H₄ | —(CH₂)₃— | —CONH— | 4-hydroxy-3-methyl-5-(NHCOCH₃)-phenyl with COCH₃ | Yellowish foamy product | 0.64(2H, b), 0.79~1.10(6H, s, m), 1.30(2H, b), 1.40(3H, s), 1.47~1.85(6H, m), 2.33(1H, m), 4.19(1H, s), 5.70~5.82(4H, m), 5.95~6.05(5H, m), 6.58(1H, b), 6.90~7.05(2H, m), 11.42(1H, b) |
| 50 | 4-F-C₆H₄ | 4-F-C₆H₄ | —(CH₂)₃— | —CONH— | 4-hydroxy-3-methyl-5-[CH(CH₃)₂]-phenyl with COCH₃ | Brownish oily product | 1.25(6H, m), 1.75(2H, b), 1.94(4H, b), 2.24(2H, b), 2.48(4H, b), 2.65(3H, s), 2.78(2H, b), 3.41(1H, m), 5.46(1H, s), 6.94~7.07(4H, m), 7.22~7.32(6H, m), 8.14(1H, b), 8.54(1H, d), 12.71(1H, b) |
| 51 | 4-F-C₆H₄ | 4-F-C₆H₄ | —(CH₂)₃— | —CONH— | 4-hydroxy-3-methyl-5-OCH₃-phenyl with COCH₃ | Orange foamy product | 1.81(2H, b), 1.90~2.15(3H, m), 2.30~2.60(5H, m), 2.64(3H, s), 2.87(2H, b), 3.50(1H, m), 3.81(1H, s), 5.47(1H, s), 6.91~7.07(4H, m), 7.21~7.31(4H, m), 8.22(1H, b), 8.36(1H, d), 12.42(1H, b) |
| 52 | 4-F-C₆H₄ | 4-F-C₆H₄ | —(CH₂)₃— | —CONH— | 4-COOCH₃-phenyl | Colorless foamy product | 1.98(2H, b), 2.05~2.39(4H, m), 2.75(2H, t), 2.92(2H, t), 3.05(4H, b), 3.72(1H, m), 3.89(3H, s), 5.42(1H, s), 6.99~7.08(4H, m), 7.22~7.29(4H, m), 7.74~8.00(4H, m), 9.92(1H, b) |
| 53 | 4-F-C₆H₄ | 4-F-C₆H₄ | —(CH₂)₃— | —CONH— | 4-COOH-phenyl | Colorless crystal m.p. 168~169° C. | |

TABLE 5-continued

| Example | Ar¹ | Ar² | X | Y | Z | Property (m.p.) | NMR spectrum (CDCl₃, δ) |
|---|---|---|---|---|---|---|---|
| 54 |  | 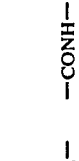 | —(CH₂)₃— | —CONH— |  | Yellowish foamy product | 1.76~2.16(6H, m), 2.25(2H, b), 2.62(3H, s), 2.70(2H, b), 2.81(2H, b), 3.02(2H, b), 3.72(1H, m), 5.59(1H, s), 6.91(1H, d), 7.17~7.72(9H, m), 8.30(1H, d), 8.52(1H, m), 9.62(1H, b), 12.08(1H, s) |
| 55 |  | 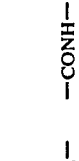 | —(CH₂)₃— | —CONH— |  | Brownish foamy product | 1.74(2H, b), 1.83~2.00(4H, m), 2.15(2H, b), 2.24(3H, s), 2.45(4H, m), 2.59(3H, s), 2.80(2H, b), 3.50(1H, m), 5.60(1H, s), 7.12~7.72(8H, m), 7.99(1H, m), 8.51(1H, m), 8.94(1H, b), 12.40(1H, b) |
| 56 |  | 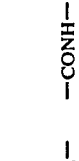 | —(CH₂)₃— | —CONH— |  | Yellowish foamy product | 1.60~1.98(6H, b), 2.12(2H, b), 2.30~2.52(4H, m), 2.64(3H, s), 2.71(2H, b), 3.49(1H, m), 5.60(1H, s), 7.08~7.74(8H, m), 8.31(1H, b), 8.50(2H, m), 12.60(1H, b) |
| 57 |  | 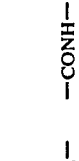 | —(CH₂)₅— | —CONH— |  | Pale brown foamy product | 1.35(2H, b), 1.51(2H, b), 1.71(4H, b), 1.88(2H, b), 2.12(2H, b), 2.22~2.38(4H, m), 2.62(3H, s), 2.72(2H, b), 3.45(1H, m), 5.60(1H, s), 6.90(1H, d), 7.11~7.72(9H), 8.24(1H, d), 8.50(1H, m) |
| 58 |  | 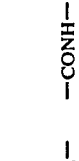 | —(CH₂)₃— | —CONH— |  | Yellowish foamy product | 1.75~2.22(6H, m), 2.49(2H, b), 2.60(3H, s), 2.62(4H, b), 2.89(2H, b), 3.61(1H, m), 5.60(1H, s), 7.18~7.77(10H, m), 8.51(1H, b), 9.42(1H, b), 12.47(1H, b) |

Example 59

Synthesis of
1-{3-[N-(6-methoxy-2-methoxycarbonylchromon-8-yl)carbamoyl]propyl}-4-(4-chlorophenyl)-2-pyridylmethoxy]piperidine

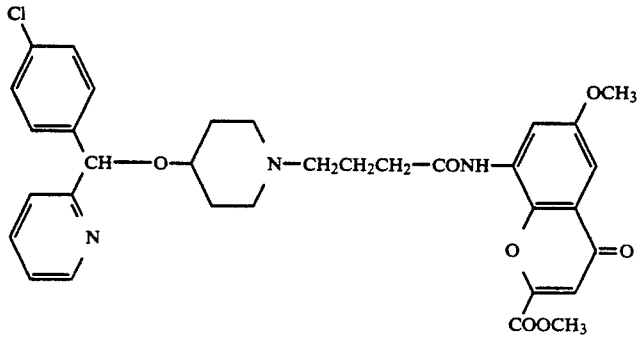

a) To 7.17 g (33.95 mmol) of 2-hydroxy-5-methoxy-3-nitroacetophenone synthesized in the same manner as in Example 48-a) were added 50 ml of methanol and 9.02 g (76.38 mmol) of dimethyl oxalate, and to the mixture was added dropwise a solution of 26.20 g (135.8 mmol) of sodium methylate (a 28% methanol solution) diluted with 50 ml of methanol at room temperature while stirring. Simultaneously with the dropwise addition, a red gel-like product was precipitated. After completion of the dropwise addition, the mixture was stirred at room temperature for 2 hours. The reaction mixture was allowed to stand overnight and then filtered. The obtained red crystals were shaken with 600 ml of chloroform, 500 ml of water and 50 ml of 1N hydrochloric acid, and the organic layer was concentrated under reduced pressure. To the residue were added 80 ml of methanol and 2 ml of conc. hydrochloric acid, and the mixture was refluxed for about 30 minutes. After cooling at ambient temperature, the precipitates were filtred off to obtain 7 g of yellow crystals. The crystals were further recrystallized from 600 ml of methanol to obtain 3.00 g (yield: 32%) of 6-methoxy-2-methoxycarbonyl-8-nitrochromone as yellow needle crystals.

Melting point: 192° to 193° C.
MS spectrum (EI)m/e: 279 (M+).
(CI)m/e: 280 (M+ +1).
$^1$H-NMR spectrum (CDCl$_3$, δ):
3.98 (3 H, s), 4.02 (3 H, s), 7.16 (1 H, s), 7.83 (1 H, d), 7.95 (1 H, d).

b) In 50 ml of acetic acid was dissolved 2.98 g (10.67 mmol) of 6-methoxy-2-methoxycarbonyl-8-nitrochromone, and the mixture was stirred at room temperature for 1.5 hour in the presence of 1.0 g of 5% palladium carbon while bubbling hydrogen gas thereinto. After completion of the reaction, the inorganic substance was filtered off, and the filtrate was concentrated under reduced pressure. The residue was dissolved in 100 ml of chloroform, and washed with an aqueous saturated sodium hydrogen carbonate solution. The organic layer was concentrated under reduced pressure to obtain 2.31 g (yield: 87%) of 8-amino-6-methoxy-2-methoxycarbonylchromone as brown crystals.

Melting point: 145° to 147° C.
MS spectrum (EI)m/e: 249 (M+).
(CI)m/e: 250 (M+ +1).

c) To 2.0 g (5.14 mmol) of 4-(4-[(4-chlorophenyl)-2-pyridylmethoxy]piperidinyl)butanoic acid dissolved in 20 ml of dichloromethane was added 1.27 g (6.17 mmol) of dicyclohexylcarbodiimide, and the mixture was stirred at 0° C. for 30 minutes. To the reaction mixture was added 1.54 g (6.18 mmol) of 8-amino-6-methoxy-2-methoxycarbonylchromone, and the mixture was further stirred at 0° C. for 3 hours. The reaction mixture was allowed to stand at room temperature overnight and then concentrated under reduced pressure. To the residue was added ethyl acetate, and the insolubles were filtered off. The filtrate was concentrated under reduced pressure, and the residue was applied to silica gel column chromatography using a mixed solvent of chloroform and methanol in a volume ratio of 20:1 as an eluent to obtain 0.50 g (yield: 17%) of 1-(3-[N-(6-methoxy-2-methoxycarbonylchromon-8-yl)carbamoyl]propyl)-4-[(4-chlorophenyl)-2-pyridylmethoxy]piperidine as a brown foamy product.

MS spectrum (EI)m/e: no (M+) peak.
(CI)m/e: 620 (M+ +1).
$^1$H-NMR spectrum (CDCl$_3$, δ):
1.68 (2 H, b), 1.77–2.20 (6 H, m), 2.45 (2 H, t), 2.57 (2 H, t), 2.74 (2 H, b), 3.44 (1 H, m), 3.87 (3 H, s), 3.98 (3 H, s), 5.56 (1 H, s), 7.09 (1 H, s), 7.11–7.74 (8 H, m), 8.49 (1 H, d), 8.51 (1 H, m), 8.65 (1 H, b).

EXAMPLES 60 and 61

The following compounds were synthesized according to the method in Example 59.

TABLE 6

Ar¹\
  \\\
   CH—O—[piperidine]—N—X—Y—Z\
  /\
Ar²

| Example | Ar¹ | Ar² | X | Y | Z | Property (m.p.) | NMR spectrum (CDCl₃, δ) |
|---|---|---|---|---|---|---|---|
| 60 | 4-F-C₆H₄— | 4-F-C₆H₄— | —(CH₂)₃— | —CONH— | dimethyl-CH(CH₃)₂ substituted aryl with O-CH=C(COOCH₃) chromone group | Orange foamy product | 1.24~1.31(6H, m), 1.98(2H, b), 2.29(4H, b), 2.85(2H, t), 2.96~3.21(5H, m), 3.72(1H, m), 3.99(1H, s), 5.41(1H, s), 6.95~7.11(5H, m), 7.20~7.29(4H, m), 7.78(1H, d), 8.41(1H, d), 9.27(1H, b) |
| 61 | 4-Cl-C₆H₄— | 2-pyridyl— | —(CH₂)₃— | —CONH— | CH₃ substituted aryl with O-CH=C(COOCH₃) chromone group | Yellowish foamy product | 1.68(2H, b), 1.78~2.01(4H, m), 2.05~2.27(4H, m), 2.49(3H, s), 2.58(2H, t), 2.74(2H, b), 3.44(1H, m), 3.98(3H, s), 5.58(1H, s), 7.07~7.72(9H, m), 8.47~8.55(2H, m), 8.64(1H, b) |

EXAMPLE 62

Synthesis of 1-{3-{4-[N-(1,2,3,4-tetrazol-5-yl)carbamoyl]phenoxy}propyl}-4-[(4-chlorophenyl)-2-pyridylmethoxy]piperidine

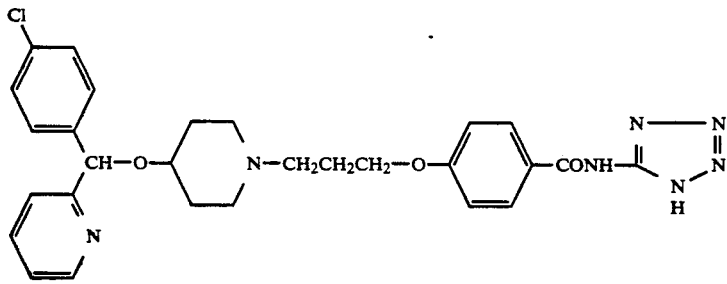

To 0.84 g (1.75 mmol) of 1-[3-(4-carboxyphenoxy)propyl]-4[(4-chlorophenyl)-2-pyridylmethoxy]piperidine dissolved in 8 ml of dichloromethane was added dropwise 1.5 ml of oxalyl chloride under cooling in an ice bath. The mixture was stirred at 0° C. for 0.5 hour and then at room temperature for 0.5 hour, and concentrated under reduced pressure. The residue was added dropwise to a mixed solution of 0.15 g (1.76 mmol) of 5-amino-1,2,3,4-tetrazole dissolved in 10 ml of dichloromethane and 5 ml of pyridine under cooling in an ice bath. After completion of the dropwise addition, the mixture was stirred at 0° C. for 2 hours and then at room temperature for 2 hours, and concentrated under reduced pressure. The residue was applied to silica gel column chromatography using a mixed solvent of chloroform and methanol in a volume ratio of 20:1 and then using a mixed solvent of chloroform, methanol and 28% aqueous ammonia in a volume ratio of 100:10:1 as eluents to obtain 0.54 g (yield: 57%) of 1-{3-{4-[N-(1,2,3,4-tetrazol-5-yl)carbamoyl]phenoxy}propyl}-4-[(4-chlorophenyl)-2-pyridylmethoxy]piperidine as an orange foamy product.

MS spectrum (EI)m/e: no (M⁺) peak.

(CI)m/e: 548 (M⁺+1).

¹H-NMR spectrum (CDCl₃, δ):
2.01-2.21 (2 H, m), 2.23-2.49 (4H, m), 3.28 (1 H, m), 3.29-3.83 (6 H, m), 3.86 (1 H, s), 4.00 (1 H, s), 4.09 (2 H, m), 5.59 (1 H, s), 6.81 (1 H, d), 6.87 (1 H, d), 7.17-7.48 (6 H, m), 7.67-7.77 (1 H, m), 7.91-7.99 (2 H, m), 8.51 (1 H, d).

EXAMPLES 63 to 66

The following compounds were synthesized according to the method in Example 62.

EXAMPLES 67

Synthesis of 1-{3-{4-(1,2,3,4-tetrazol-5-yl)phenoxy]-propyl}-4-diphenylmethoxypiperidine

TABLE 7

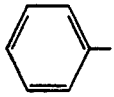

| Example | Ar¹ | Ar² | X | Y | Z | Property (m.p.) | NMR spectrum (CDCl₃, δ) |
|---|---|---|---|---|---|---|---|
| 63 | 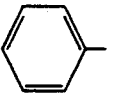 | 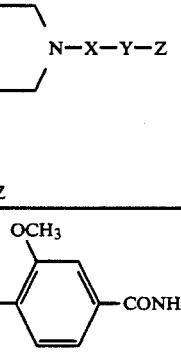 | —(CH₂)₃— | —O— | 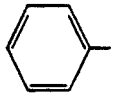 | Colorless crystal m.p. 194~195° C. | |
| 64 | 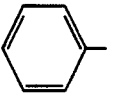 | 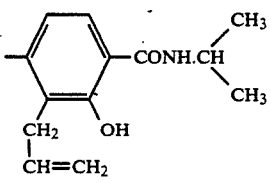 | —(CH₂)₃— | —O— | 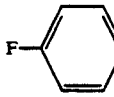 | Orange foamy product | 1.26(6H, m), 1.95(2H, b), 2.23(4H, b), 2.20~3.02(6H, m), 3.51(2H, d), 3.69(1H, m), 4.07(2H, t), 4.25(1H, m), 4.95(2H, m), 5.49(1H, s), 6.00(1H, m), 6.37(1H, d), 7.21~7.35(10H, m), 12.85(1H, b) |
| 65 | 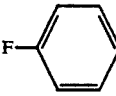 | 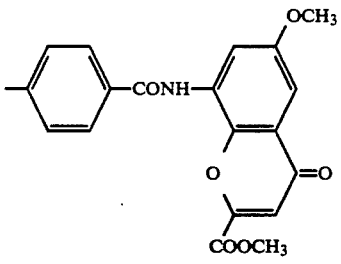 | —(CH₂)₃— | —O— | 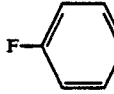 | Dark orange foamy product | 1.99(2H, b), 2.37(4H, b), 3.05(6H, b), 3.72(1H, b), 3.92(3H, s), 4.05(3H, s), 4.17(2H, t), 5.44(1H, s), 6.95~7.14(6H, m), 7.22~7.32(6H, m), 7.87~7.98(2H, m), 8.60(1H, d), 8.74(1H, b) |
| 66 | 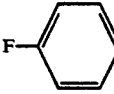 | 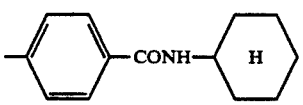 | —(CH₂)₃— | —O— |  | Colorless foamy product | 0.83~1.00(2H, m), 1.03~1.41(4H, m), 1.43~2.20(12H, m), 2.45(2H, t), 2.73(2H, b), 3.38~3.55(2H, m), 4.04(2H, m), 5.48(1H, s), 6.05(1H, d), 6.82~7.04(6H, m), 7.23~7.31(5H, m), 7.52(1H, d) |

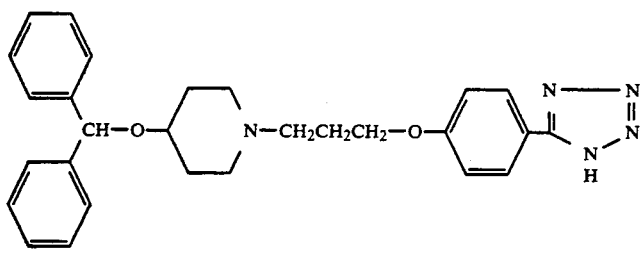

1.67 g (3.92 mmol) of 1-[3-(4-cyanophenoxy)propyl]-4diphenylmethoxypiperidine dissolved in 15 ml of dimethylformamide was added 1.26 g (23.6 mmol) of ammonium chloride, and the mixture was stirred at 45° C. for 15 minutes. Subsequently, 1.02 g (15.7 mmol) of sodium azide was added to the mixture, and the mixture was stirred at 100° C. to 110° C. for 12 hours. After completion of the reaction, the reaction mixture was allowed to cool to 70° C., and a solution of 1.6 ml of conc. hydrochloric acid diluted with 50 ml of water was added. After the mixture was allowed to cool to 35° C., 10 ml of n-hexane and 1.35 g (19.6 mmol) of sodium nitrite in 5 ml of water were added to the mixture to give vigorous gas evolution and then an amber viscous product was liberated. After the supernatant was removed by decantation, 50 ml of ethyl acetate was added to the residual amber viscous product, and the mixture was shaken vigorously. The precipitated crystals were filteref off and washed sufficiently with ethyl acetate to obtain 1.20 g (yield: 65%) of 1-{3-[4-(1,2,3,4-tetrazol-5-yl)phenoxy]propyl}-4-diphenylmethoxypiperidine as pale brown crystals.

Melting point: 167° to 171° C.
MS spectrum (EI)m/e: no (M+) peak.
(CI)m/e: 470 (M+ +1).

EXAMPLES 68 to 70

The following compounds were synthesized according to the method in Example 67.

TABLE 8

| Example | Ar¹ | Ar² | X | Y | Z | Property (m.p.) | NMR spectrum (CDCl₃, δ) |
|---|---|---|---|---|---|---|---|
| 68 | phenyl | phenyl | —(CH₂)₃— | —O— | (chromone-tetrazole, CH₂CH=CH₂ substituent) | Pale yellowish crystal m.p. 218~220° C. | |
| 69 | 4-F-phenyl | 4-F-phenyl | —(CH₂)₃— | —O— | (phenyl-tetrazole) | Pale brownish crystal m.p. 188~190° C. | |
| 70 | 4-Cl-phenyl | pyridyl | —(CH₂)₃— | —O— | (phenyl-tetrazole) | Brownish foamy product | 2.21(4H, b), 2.74~3.91(7H, m), 4.55(2H, t), 5.70(1H, s), 7.06(2H, m), 7.28~8.09(9H, m), 8.59(1H, b) |

We claim:

1. A diarylmethoxypiperidine compound represented by the formula (I):

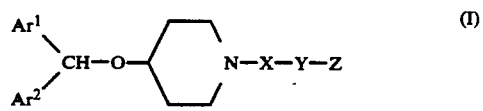

(I)

wherein
Ar¹ and Ar² each represent a phenyl group, a phenyl group substituted by a halogen atom, or a pyridyl group;
X represents an alkylene group having 3 carbon atoms or a group having

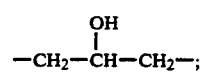

Y represents an oxygen atom or a group having —CONH—; and

Z represents a 4-(tetrazol-5-yl)-phenyl, 3-acetyl-2-hydroxy -5-methylphenyl, 4-acetyl-3-hydroxy-2-n-propylphenyl, 4-[N-(tetrazol -5-yl)carbamoyl]phenyl or 6-methoxy-2-methoxycarbonyl-chromon -8-yl group.

2. A diarylmethoxypiperidine compound represented by the formula (I):

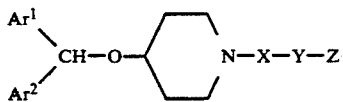

wherein
Ar$^1$ and Ar$^2$ each represent a phenyl group, a phenyl group substituted by a halogen atom, or a pyridyl group;

X represents an alkylene group having 2 or 3 carbon atoms;

Y represents an oxygen atom or a group having —CONH—; and

Z represents a 4-t-butylphenyl, 4-methyoxycarbonylphenyl, 4-(tetrazol -5-yl)phenyl, 4-acetyl-2-methoxyphenyl, 4-acetyl-2,6-dimethoxyphenyl, 3-hydroxxy-4-methoxycarbonylphenyl, 4-acetyl-2-allkyl -3-hydroxyphenyl, 2-methoxy-4-methoxycarbonylphenyl, 2-methoxycarbonyl -6-isopropylchromon-8-yl, 8-allyl-4-methylcoumarin-7-yl, 6-methoxycoumarin-7-yl, 4-carboxyphenyl or 4-cyanophenyl group.

3. The diarylmethoxypiperidine compound according to claim 2, wherein Z is a 4-methoxycarbonylphenyl, 4-acetyl-2-methoxyphenyl or 4-carboxyphenyl group.

4. The diarylmethoxypiperidine compound according to claim 2, wherein Z is a 4-acetyl-2-methoxyphenyl group.

5. A diarylmethoxypiperidine compound wherein said compound is:

1-[3-(4-acetyl-3-hydroxy-2-n-propylphenoxy)propyl]-4-[(4-chlorophenyl-2-pyridylmethoxy]piperidine.fumarate, 1-{[3-(4-acetyl-3-hydroxyl-2-n-propylphenoxy)-2-hydroxyl]propyl}-4-[bis(4-fluorophenyl)methoxy]piperidine.fumarate, 1-{3-{N-[(3-acetyl-2-hydroxy-5-methyl)phenyl]carbamoyl}propyl}-4-[(4-chlorophenyl)-2-pyridylmethoxy]piperidine, 1-{3-[N-(6-methoxy-2-methoxycarbonylchromon-8-yl)carbamoyl]propyl}-4-[(4-chlorophenyl)-2-pyridylmethoxy]piperidine, 1-{3-{4-[N-(1,2,3,4-tetrazol-5-yl)carbamoyl]phenoxy}propyl}-4-[(4-chlorophenyl)-2-pyridylmethoxy]piperidine or 1-{3-[4-(1,2,3,4-tetrazol-5-yl)phenoxy]propyl}-4-diphenylmethoxypiperidine.

6. A diarylmethoxypiperidine compound wherein said compound is:

1-[3-(4-acetyl-2-methoxyphenoxy)propyl]-4-(diphenylmethoxy)piperidine,

1-[3-(4-methyoxycarbonyl-2-methoxyphenoxy)propyl]-4-(diphenylmethoxy)piperdine,

1-[3-(3-hydroxy-4-methoxycarbonylphenoxy)propyl]-4-(diphenylmethoxy)piperidine,

1-[3-(4-acetyl-2,6-dimethoxyphenoxy)propyl]-4-(diphenylmethoxy)piperidine,

1-[3-(8-allyl-4-methylcoumarin-7yloxy)propyl]-4-(diphenylmethoxy)piperidine,

1-[3-(6-methoxycoumarin-7-yloxy)propyl]-4-(diphenylmethoxy)piperidine,

1-[3-(4-cyanophenoxy)propyl]-4-(diphenylmethoxy)piperidine,

1-[-(4-tert-butylphenoxy)propyl]-4-(diphenylmethoxy)piperidine,

1-[3-(4-methoxycarbonylphenoxy)propyl]-4-(diphenylmethoxy)piperidine,

1-[3-(4-acetyl-2-methoxyphenoxy)propyl]-4-[bis(4-fluorophenyl)methoxy]piperidine, 1-[3-(4-methoxycarbonylphenoxy)propyl]-4-[bis(4-fluorophenyl)methoxyl]piperidine, 1-[3-(4-carboxyphenyl)propyl]-4-[bis(4-fluorophenyl)methoxy]piperidine, 1-[3-(tert-butylphenoxy)propyl]-4-[bis(4-fluorophenyl)methoxy]piperidine, 1-{3-[N-(6-isopropyl-2-methoxycarbonylchromon-8yl)carbamoyl]propyl}-4-[bis(4-fluorophenyl)methoxy]piperidine, 1-[3-(4-acetyl-2-allyl-3-hydroxyphenoxy)propyl]-4-[(4-chlorophenyl)-2-pyridylmethoxy]piperidine, 1-[3-(4-acetyl-2-methoxyphenoxy)propyl]-4-[(4-chlorophenyl)-2-pyridylmethoxy]piperidine, or 1-{3-[4-(1,2,3,4-tetrazol-5-yl)phenoxy]ethyl}-4-[(4-chlorophenyl)-2-pyridylmethoxy]piperidine.

7. The diarylmethoxypiperidine compound according to claim 6, wherein said compound is:

1-[3-(4-acetyl-2-methoxyphenoxy)propyl]-4-(diphenylmethoxy)piperidine,

1-[3-(4-acetyle-2-methoxyphenoxy)propyl]-4-[bis(4-fluorophenyl)methoxy]piperidine, 1-[3-(4-methoxycarbonylphenoxy)propyl]-4-[bis(4-fluorophenyl)methoxy]piperidine, or 1-[3-(4-acetyl-2-methoxyphenoxy)propyl]-4-[(4-chlorophenyl) -2-pyridylmethoxyl]piperidine.

* * * * *

UNITED STATES PATENT AND TRADEMARK OFFICE
CERTIFICATE OF CORRECTION

PATENT NO. : 5,225,559
DATED : July 06, 1993
INVENTOR(S) : Jun'ichiro Kita et al.

Page 1 of 3

It is certified that error appears in the above-indentified patent and that said Letters Patent is hereby corrected as shown below:

Claim 1, column 81, line 2, change "hydroxy -5" to --hydroxy-5--.

Claim 1, column 81, line 3, change "tetrazol -5-yl" to --tetrazol-5-yl--.

Claim 2, column 81, line 25, change "tetrazol -5-yl" to --tetrazol-5-yl--.

Claim 2, column 81, line 27, change "hydroxxy" to --hydroxy--.

*Claim 2, column 81, line 28, change "allkyl -3" to --allyl-3--.

Claim 2, column 81, line 29, change "carbonyl -6" to --carbonyl-6--.

UNITED STATES PATENT AND TRADEMARK OFFICE
CERTIFICATE OF CORRECTION

PATENT NO. : 5,225,559
DATED : July 06, 1993
INVENTOR(S) : Jun'ichiro Kita et al.

It is certified that error appears in the above-indentified patent and that said Letters Patent is hereby corrected as shown below:

Claim 5, column 81, line 44, after "4-chlorophenyl" insert --)--.

Claim 5, column 81, line 46, change "hydroxyl" to --hydroxy--.

*Claim 5, column 81, line 47, change "hydroxyl" to --hydroxy--.

Claim 6, column 82, line 22, change "1-[-4" to --1-[3-4--.

Claim 6, column 82, line 25, change ")piperidine" to --)-piperidine--.

UNITED STATES PATENT AND TRADEMARK OFFICE
CERTIFICATE OF CORRECTION

PATENT NO. : 5,225,559

DATED : July 06, 1993

INVENTOR(S) : Jun'ichiro Kita et al.

It is certified that error appears in the above-indentified patent and that said Letters Patent is hereby corrected as shown below:

Claim 6, column 82, line 34, change "8yl)" to --8-yl)--.

Claim 7, column 82, last line, change ")  -2-pyridylmethoxyl" to --)-2-pyridylmethoxy--.

Signed and Sealed this

Eighth Day of November, 1994

Attest:

BRUCE LEHMAN

Attesting Officer

Commissioner of Patents and Trademarks